United States Patent
Helal et al.

(10) Patent No.: US 11,124,530 B1
(45) Date of Patent: Sep. 21, 2021

(54) ZIRCONIUM METAL-ORGANIC FRAMEWORK AND A METHOD OF DETECTING COPPER AND CHROMATE IONS

(71) Applicant: KING FAHD UNIVERSITY OF PETROLEUM AND MINERALS, Dhahran (SA)

(72) Inventors: Aasif Helal, Dhahran (SA); M. Nasiruzzaman Shaikh, Dhahran (SA)

(73) Assignee: KING FAHD UNIVERSITY OF PETROLEUM AND MINERALS, Dhahran (SA)

(*) Notice: Subject to any disclaimer, the term of this patent is extended or adjusted under 35 U.S.C. 154(b) by 0 days.

(21) Appl. No.: 16/660,411

(22) Filed: Oct. 22, 2019

(51) Int. Cl.
| | |
|---|---|
| C07F 7/00 | (2006.01) |
| C07D 249/18 | (2006.01) |
| G01N 33/18 | (2006.01) |
| G01N 21/64 | (2006.01) |

(52) U.S. Cl.
CPC ............ C07F 7/00 (2013.01); G01N 21/6428 (2013.01); G01N 33/1813 (2013.01)

(58) Field of Classification Search
CPC ...... C07F 7/00; C07D 249/18; G01N 33/1813
See application file for complete search history.

(56) References Cited

FOREIGN PATENT DOCUMENTS

| | | |
|---|---|---|
| CN | 108295825 A | 7/2018 |
| CN | 109569520 A | 4/2019 |
| CN | 109569521 A | 4/2019 |
| WO | WO 2019/046404 A1 | 3/2019 |

OTHER PUBLICATIONS

Katritzky, Chemistry of Benzotriazole Part 3—Aminoalkylation of Benzotriazole, J. Chem. Soc. Perkin Trans. I, 1987, vol. 4, p. 799-804 (Year: 1987).*

Shibiao Wu,et al. Adsorption of Cr(VI) on nano Uio-66-$NH_2$ MOFs in water, Adsorption of Cr(VI) on nano Uio-66-NH2 MOFs in water: Environmental Technology: vol. 39, No. 15, https://doi.org/10.1080/09593330.2017.1344732, 1 page.

Yang Wang, et al., A metal-organic framework and conducting polymer based electrochemical sensor for high performance cadmium ion detection, Journal of Materials Chemistry A, Issue 18, 2017, https://pubs.rsc.org/en/content/articlelanding/2017/ta/c7ta01066d#!divAbstract, 2 pages.

Juan Xiao, et al., Crystalline Structural Intermediates of a Breathing Metal-Organic Framework That Functions as a Luminescent Sensor and Gas Reservoir, Chemistry – A European Journal / vol. 19, Issue 6, https://doi.org/10.1002/chem.201203515, 1 page.

* cited by examiner

*Primary Examiner* — Karen Cheng
(74) *Attorney, Agent, or Firm* — Oblon, McClelland, Maier & Neustadt, L.L.P.

(57) ABSTRACT

A zirconium metal-organic framework, which is a coordination product formed between zirconium ion clusters and a linker that links together adjacent zirconium ion clusters, wherein the linker is of formula (I)

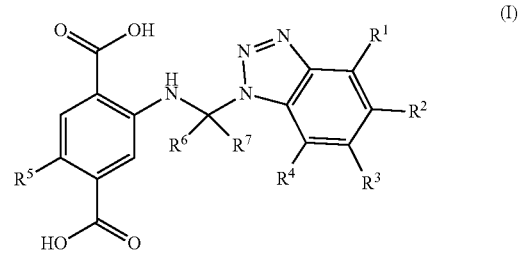

wherein $R^1$ to $R^4$ are independently hydrogen, an optionally substituted alkyl, an optionally substituted aryl, an optionally substituted arylalkyl, an optionally substituted alkoxy, a hydroxyl, a carboxyl, a halo, a nitro, or a cyano, $R^5$ is hydrogen, an optionally substituted alkyl, an optionally substituted alkoxy, an amino, a hydroxyl, a carboxyl, a halo, a nitro, or a cyano, and $R^6$ and $R^7$ are independently a hydrogen or an optionally substituted alkyl group having 1 to 4 carbon atoms. A method of detecting copper cations and/or chromate anions in a fluid sample with zirconium metal-organic framework.

20 Claims, 7 Drawing Sheets

ZIRCONIUM METAL-ORGANIC FRAMEWORK AND A METHOD OF DETECTING COPPER AND CHROMATE IONS

BACKGROUND OF THE INVENTION

Field of the Invention

The present invention relates to a copper/chromate selective fluorescent chemosensor, particularly a zirconium metal-organic framework (Zr-MOF), and methods of detecting copper/chromate ions in a fluid sample with the Zr-MOF.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Even in low concentrations, copper can affect enzyme activity owing to its redox-active nature. See Gaetke, L. M.; Chow-Johnson, H. S.; Chow, C. K. *Arch. Toxicol*, 2014, 88, 1929-1938, incorporated herein by reference in its entirety. Moreover excessive use of copper materials in the manufacturing, medicinal and chemical industries have made it a heavy metal pollutant. This has led to excessive accretion of copper in the human body that might cause gastrointestinal disturbance, damage to the liver and kidney, hepatolenticular degeneration (Wilson's disease), Alzheimer's diseases, Menkes syndrome, neutropenia and myelopathy. See Cotruvo, Jr., J. A.; Aron, A. T.; Ramos-Torres, K. M.; Chang, C. J. *Chem. Soc. Rev.*, 2015, 44, 4400-4414, incorporated herein by reference in its entirety. Thus the U.S. Environmental Protection Agency (EPA) has set the limit of copper concentration in drinking water to be 1.3 ppm (~20 µM). See 2018 Edition of the Drinking Water Standards and Health Advisories Tables, EPA 822-F-18-001 Office of Water U.S. Environmental Protection Agency Washington, D.C., incorporated herein by reference in its entirety. It is therefore necessary to develop highly selective and sensitive methods for the detection of copper ion in aqueous fluids. Several detection techniques for copper ions have been reported, including inductively coupled plasma mass spectrometry (ICP-MS) and inductively coupled plasma atomic emission spectrometry (ICP-AES), activated carbon adsorption, natural zeolite adsorption, and membrane technology. See S. C. Wang and M. J. Starink, Int. Mater. Rev., 2013, 50, 193; M. Kobya, E. Demirbas, E. Senturk and M. Ince, Bioresour. Technol., 2005, 96, 1518; and Dhal, B.; Thatoi, H. N.; Das, N. N.; Pandey, B. D. J. Hazard. Mater. 2013, 250-251, 272-291, each incorporated herein by reference in their entirety. However, these methods have their own disadvantages such as low selectivity, tedious and troublesome analysis methods, and the need for expensive instrumentation for carrying out the analysis.

Chromium as an oxidant has wide-ranging industrial applications such as in chromium electroplating, metallurgy, pigment production, leather tanning, detergent manufacturing, welding, steel manufacturing, and wood preservation. See Gu, T. Y.; Dai, M.; Young, D. J.; Ren, Z. G.; Lang, J. P. Inorg. Chem. 2017, 56, 466-4678, incorporated herein by reference in its entirety. Excessive accumulation of Cr(III) causes binding with DNA resulting in cell mutation or formation of malignant cells. See Liu, J. J.; Ji, G. F.; Xiao, J. N.; Liu, Z. L. Inorg. Chem. 2017, 56, 4197-4205; and R. Rakhunde, L. Deshpande, H. D. Juneja, Chemical speciation of chromiuminwater: a review, Crit. Rev. Environ. Sci. Technol. 42 (2012) 776-810, each incorporated herein by reference in their entirety. On the other hand, Cr(VI) is a carcinogenic species with higher oxidation potential and a size which allows for diffusion through cell membranes. See Mohandossa S, Sivakamavallib J, Vaseeharanb B, Stalina T. *Sens Actuators B* 2016; 234:300-15, incorporated herein by reference in its entirety. Chromate ions can also cause allergic reactions in humans and prolonged exposure results in chrome ulcer, contact dermatitis, and irritant dermatitis. See Prakash, A.; Chandra, S.; Bahadur, D. Carbon 2012, 50, 4209-4219, incorporated herein by reference in its entirety. Several techniques have been employed for the detection of these chromium species such as inductively coupled plasma mass spectrometry, atomic absorption spectrometry, electrochemistry, and chromatography. See Feldman, F. J.; Knoblock, E. C.; Purdy, W. C. Anal. Chim. Acta 1967, 38, 489-497; and Yan Bai, Yibo Dou, Lin-Hua Xie, William Rutledge, Jian-Rong Li Hong-Cai Zhou *Chem. Soc. Rev.*, 2016, 45, 2327-2367, each incorporated herein by reference in their entirety. However, these methods are time consuming, expensive, require significant sample preconditioning, and rely on expensive and complicated instrumentation. In light of these drawbacks, fluorescence-based chemical sensors are gaining popularity.

Metal-organic frameworks (MOFs) are a class of porous, crystalline materials that have an extraordinary high surface area with tunable pore size, and functionalizable internal surface properties. See Furukawa, H.; Cordova, K. E.; O'Keeffe, M.; Yaghi, O. M. The Chemistry and Applications of Metal-Organic Frameworks. Science 2013, 341, 123044, incorporated herein by reference in its entirety. Due to their porous structure and high surface area, MOFs have been extensively used for the capture and storage of carbon dioxide, hydrogen and methane. See Kenji Sumida, David L. Rogow, Jarad A. Mason, Thomas M. McDonald, Eric D. Bloch, Zoey R. Herm, Tae-Hyun Bae, and Jeffrey R. Long Chem. Rev. 2012, 112, 724-781; and Hao Li, Kecheng Wang, Yujia Sun, Christina T. Lollar, Jialuo Li, Hong-Cai Zhou Materials Today, 2018, 21, 108-121, each incorporated herein by reference in their entirety. The pore structures of these structures can be engineered by using functionalized linkers for different potential applications. See Trickett, C. A.; Helal, A.; Al-Maythalony, B. A.; Yamani, Z. H.; Cordova, K. E.; Yaghi, O. M. *Nat Rev Mater.* 2017, 2, 17045, incorporated herein by reference in its entirety. The functionalization of the linkers can be performed using postsynthetic modification (PSM), postsynthetic exchange (PSE), or by direct solvothermal synthesis using presynthetically functionalized organic linkers, in order to engineer the surface properties of the MOF. See Deria, P.; Mondloch, J. E.; Karagiaridi, O.; Bury, W.; Hupp, J. T.; Farha, O. K. Chem. Soc. Rev. 2014, 43, 5896-5912; Wang, Z.; Cohen, S. M. Chem. Soc. Rev. 2009, 38, 1315-1329; and Cohen, S. M. J. Am. Chem. Soc. 2017, 139, 2855-2863, each incorporated herein by reference in their entirety.

In most zirconium-based MOFs, the fluorescence originates from the organic linkers. Since the benzene ring produces very little photoluminescence, it can be targeted for functionalization to produce strong emissions as well as for forming binding sites for cations and anions. For example, the benzene ring of the 1,4-benzenedicarboxylate (BDC) linker in MOF UiO-66 (University of Oslo) can be functionalized without disturbing the high thermal and chemical stability of the MOF. See A. Kumar, H.-S. Kim, Spectrochim. Acta. A 148 (2015) 250-254, incorporated herein by reference in its entirety.

In view of the forgoing, there is a need for effective, sensitive, and selective fluorescent chemosensors for the detection of copper and/or chromate ions, which are easy and inexpensive to make, and which are can operate under a broad range of pH values and temperatures.

SUMMARY OF THE INVENTION

Accordingly, it is one object of the present invention to provide a zirconium metal-organic framework (Zr-MOF) for the detection of copper cations and/or chromate anions, which is highly sensitive to and selective for only copper/chromate ions, is easy to make, and which can operate under a broad range of pH values and temperatures.

It is another object of the present disclosure to provide methods for the detection of copper cations and/or chromate anions in a fluid sample using the Zr-MOF.

Thus the present disclosure provides a zirconium metal-organic framework, which is a coordination product formed between (i) zirconium ion clusters, and (ii) a linker that links together adjacent zirconium ion clusters, wherein the linker is of formula (I)

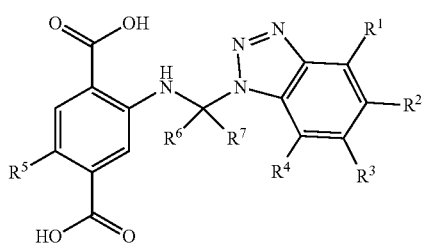

wherein $R^1$ to $R^4$ are independently hydrogen, an optionally substituted alkyl, an optionally substituted aryl, an optionally substituted arylalkyl, an optionally substituted alkoxy, a hydroxyl, a carboxyl, a halo, a nitro, or a cyano, $R^5$ is hydrogen, an optionally substituted alkyl, an optionally substituted alkoxy, an amino, a hydroxyl, a carboxyl, a halo, a nitro, or a cyano, and $R^6$ and $R^7$ are independently a hydrogen or an optionally substituted alkyl group having 1 to 4 carbon atoms.

In some embodiments, $R^1$ to $R^4$ are hydrogen.
In some embodiments, $R^5$ is hydrogen.
In some embodiments, $R^6$ and $R^7$ are hydrogen.
In some embodiments, the linker is

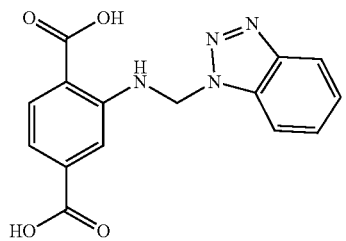

In some embodiments, the zirconium metal-organic framework has a zirconium ion to linker molecular ratio of 0.5:1 to 2:1.

In some embodiments, the zirconium ion clusters are of formula $[Zr_6O_4(OH)_4]^{12+}$.

In some embodiments, the zirconium metal-organic framework is isoreticular with metal-organic framework UiO-66.

In some embodiments, the zirconium metal-organic framework has a BET surface area of 300 to 600 $m^2/g$.

In some embodiments, the zirconium metal-organic framework has a pore volume of 0.2 to 0.4 $cm^3/g$.

In some embodiments, the zirconium metal-organic framework has a fluorescence emissions peak at 480 to 500 nm at an excitation wavelength of 360 nm.

The present disclosure also provides a method of making the zirconium metal-organic framework that involves (i) ultrasonically mixing a zirconium(IV) salt and the linker of formula (I) in a polar aprotic solvent to form a complexation mixture, (ii) adding a modulator to the complexation mixture to form a modulated mixture, and (iii) heating the modulated mixture at 100 to 150° C. for 12 to 72 hours.

In some embodiments, a concentration of the zirconium (IV) salt in the complexation mixture is 0.02 to 0.04 M, a concentration of the linker of formula (I) in the complexation mixture is 0.025 to 0.045 M, and a volume ratio of the polar aprotic solvent to the modulator in the modulated mixture is 20:1 to 60:1.

In some embodiments, the zirconium(IV) salt is $ZrCl_4$, the polar aprotic solvent is dimethylformamide, and the modulator is acetic acid.

The present disclosure also provides a method of detecting copper cations and/or chromate anions in a fluid sample, involving contacting the fluid sample with the zirconium metal-organic framework of the present disclosure to form a mixture, and measuring a fluorescence emission profile of the mixture to determine a presence or absence copper cations and/or chromate anions in the fluid sample, wherein a reduction in intensity of a fluorescence emissions peak associated with the zirconium metal-organic framework indicates the presence of copper cations and/or chromate anions in the fluid sample.

In some embodiments, 0.001 to 10 mg of the zirconium metal-organic framework is employed per 1 mL of the fluid sample during the contacting.

In some embodiments, copper cations and/or chromate anions are present in the fluid sample, and a concentration of copper cations and/or chromate anions in the fluid sample is from $1\times10^{-6}$ to $5\times10^{-1}$ M.

In some embodiments, the fluid sample is a wastewater, a tap water, a well water, or a river water, and wherein the mixture has a pH of 2 to 11 and a temperature of 10 to 70° C.

In some embodiments, copper cations and/or chromate anions are present in the fluid sample, and the fluid sample further comprises at least one cation selected from the group consisting of cobalt, iron, nickel, palladium, sodium, lead, cadmium, mercury, zinc, potassium, calcium, magnesium, strontium, rubidium, cesium, silver, aluminum, and gallium and/or at least one anion selected from the group consisting of fluoride, acetate, phosphate, chloride, bromide, iodide, sulfate, bisulfate, permanganate, and nitrate, and the method is selective for detection of the copper cations and/or chromate anions, whereby only the presence of copper cations and/or chromate anions in the mixture produces a reduction in the intensity of the fluorescence emissions peak of greater than 20%.

In some embodiments, the method further involves, after the contacting and measuring, washing the zirconium metal-organic framework with a chelating agent followed by water, and then drying, to recover/recycle the zirconium metal-organic framework.

BRIEF DESCRIPTION OF THE DRAWINGS

The foregoing paragraphs have been provided by way of general introduction, and are not intended to limit the scope of the following claims. A more complete appreciation of the invention and many of the attendant advantages thereof will be readily obtained as the same becomes better understood by reference to the following detailed description when considered in connection with the accompanying drawings, wherein:

DETAILED DESCRIPTION OF THE INVENTION

Figure 1:
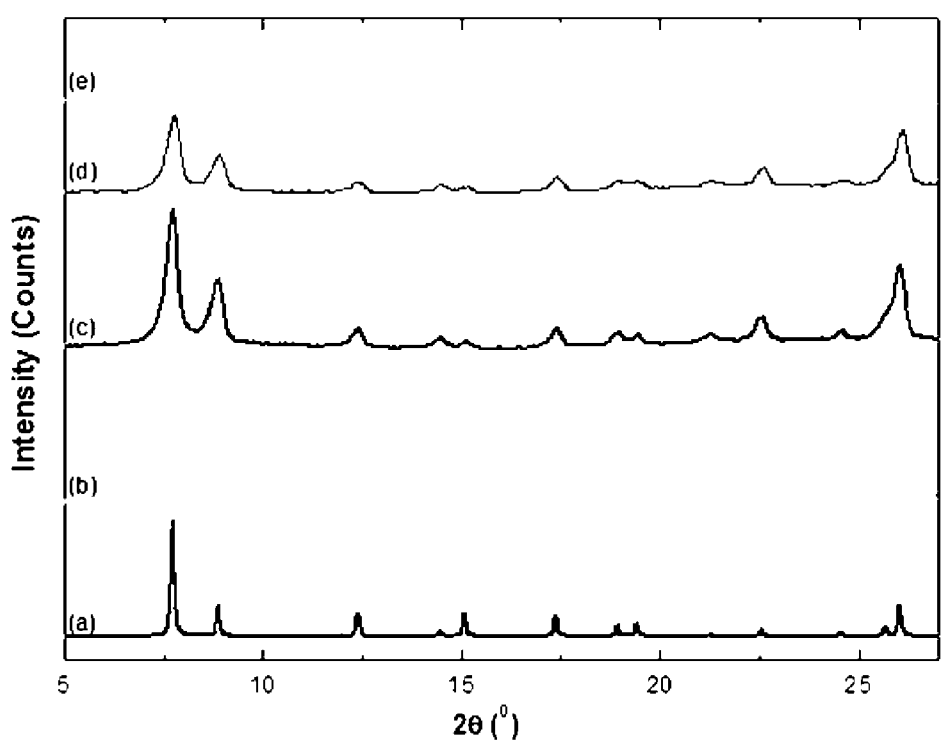
FIG. 1 illustrates powered XRD patterns of (a) UiO-66-$NH_2$ obtained from cif file, (b) UiO-66-$NH_2$ as synthesized, (c) UiO-66-NH-BT as synthesized, (d) UiO-66-NH-BT after addition of copper, (e) UiO-66-NH-BT after addition of chromate ion.

In the following description, it is understood that other embodiments may be utilized and structural and operational changes may be made without departure from the scope of the present embodiments disclosed herein.

Definitions

As used herein, "wastewater" means a water source obtained from storm drains, sedimentation ponds, runoff/outflow, landfills, as well as water sources resulting/obtained from industrial processes such as factories, mills, farms, mines, quarries, industrial drilling operations, oil and gas recovery operations, pharmaceutical processes, papermaking processes, food preparation processes, phase separation processes, washing processes, waste treatment plants, toilet processes, power stations, incinerators, spraying and painting, navigation processes, aviation processes, automotive plants, fuel cell manufacturing operations, or any other manufacturing or commercial enterprise, which comprises water and one or more compounds or materials derived from such industrial processes, including partially treated water from these sources.

As used herein, the term "fatty" describes a compound with a long-chain (linear) hydrophobic portion made up of hydrogen and anywhere from 6 to 26, 8 to 24, 10 to 22, 12 to 20, 14 to 18 carbon atoms, which may be fully saturated or partially unsaturated, and optionally attached to a polar functional group such as a hydroxyl group, an amine group, or a carboxyl group (e.g., carboxylic acid). Fatty alcohols, fatty amines, fatty acids, fatty esters, and fatty amides are examples of materials which contain a fatty portion, and are thus considered "fatty" compounds herein.

As used herein, "alkoxylated" or "alkoxylate" refers to compounds containing a (poly)ether group (i.e., (poly)oxyalkylene group) derived from reaction with, oligomerization of, or polymerization of one or more alkylene oxides having 2 to 4 carbon atoms, and specifically includes (poly)oxyethylene (derived from ethylene oxide, EO), (poly)oxypropylene (derived from propylene oxide, PO), and (poly)oxybutylene (derived from butylene oxide, BO), as well as mixtures thereof.

The phrase "substantially free", unless otherwise specified, describes a particular component being present in an amount of less than about 1 wt. %, preferably less than about 0.5 wt. %, more preferably less than about 0.1 wt. %, even more preferably less than about 0.05 wt. %, yet even more preferably 0 wt. %, relative to a total weight of the composition being discussed.

As used herein, the terms "optional" or "optionally" means that the subsequently described event(s) can or cannot occur or the subsequently described component(s) may or may not be present (e.g., 0 wt. %).

The term "alkyl", as used herein, unless otherwise specified, refers to a straight, branched, or cyclic, aliphatic fragment having 1 to 26 carbon atoms, (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, etc.) and specifically includes, but is not limited to, saturated alkyl groups such as methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, tetradecyl, pentadecyl, hexadecyl, heptadecyl, octadecyl, nonadecyl, eicosyl, guerbet-type alkyl groups (e.g., 2-methylpentyl, 2-ethylhexyl, 2-proylheptyl, 2-butyloctyl, 2-pentylnonyl, 2-hexyldecyl, 2-heptylundecyl, 2-octyldodecyl, 2-nonyltridecyl, 2-decyltetradecyl, and 2-undecylpentadecyl), as well as unsaturated alkenyl and alkynyl variants such as vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, oleyl, linoleyl, and the like, as well as cyclic alkyl groups (cycloalkyls) such as cyclopropyl, cyclobutyl, cyclopentyl, cyclohexyl, norbornyl, and adamantyl.

The term "aryl" means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, anthracenyl, indanyl, 1-naphthyl, 2-naphthyl, and tetrahydronaphthyl. The fused aryls may be connected to another group either at a suitable position on the cycloalkyl/cycloalkenyl ring or the aromatic ring.

The term "arylalkyl", as used herein, refers to a straight or branched chain alkyl moiety (as defined above) that is substituted by an aryl group (as defined above), examples of which include, but are not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "alkoxy" refers to an —O-alkyl group. Example alkoxy groups include, but are not limited to, methoxy, ethoxy, propoxy (e.g., n-propoxy and isopropoxy), and t-butoxy.

The term "halo" or "halogen" includes fluoro, chloro, bromo and iodo.

As used herein, the term "substituted" refers to at least one hydrogen atom that is replaced with a non-hydrogen group, provided that normal valencies are maintained and that the substitution results in a stable compound. When a substituent is noted as "optionally substituted", the substituent(s) are selected from alkyl, halo (e.g., chloro, bromo, iodo, fluoro), hydroxyl, alkoxy, oxo, alkanoyl, aryloxy, alkanoyloxy, amino (—NH$_2$), alkylamino (—NHalkyl), cycloalkylamino (—NHcycloalkyl), arylamino (—NHaryl), arylalkylamino (—NHarylalkyl), disubstituted amino (e.g., in which the two amino substituents are selected from alkyl, aryl or arylalkyl, including substituted variants thereof, with specific mention being made to dimethylamino), alkanoylamino, aroylamino, arylalkanoylamino, thiol, alkylthio, arylthio, arylalkylthio, alkylthiono, arylthiono, arylalkylthiono, alkylsulfonyl, arylsulfonyl, arylalkylsulfonyl, sulfonamide (e.g., —SO$_2$NH$_2$), substituted sulfonamide (e.g., —SO$_2$NHalkyl, —SO$_2$NHaryl, —SO$_2$NHarylalkyl, or cases where there are two substituents on one nitrogen selected from alkyl, aryl, or alkylalkyl), nitro, cyano, carboxy, unsubstituted amide (i.e. —CONH$_2$), substituted amide (e.g., —CONHalkyl, —CONHaryl, —CONHarylalkyl or cases where there are two substituents on one nitrogen selected from alkyl, aryl, or alkylalkyl), alkoxycarbonyl, aryl, guanidine, heterocyclyl (e.g., pyridyl, furyl, morpholinyl, pyrrolidinyl, piperazinyl, indolyl, imidazolyl, thienyl, thiazolyl, pyrrolidyl, pyrimidyl, piperidinyl, homopiperazinyl), and mixtures thereof. The substituents may themselves be optionally substituted, and may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

Throughout the specification and the appended claims, a given chemical formula or name shall encompass all isomers (stereo and optical isomers and racemates) thereof where such isomers exist. Unless otherwise indicated, all chiral (enantiomeric and diastereomeric) and racemic forms are within the scope of the disclosure. Many geometric isomers of C=C double bonds, C=N double bonds, ring systems, and the like can also be present in the compounds, and all such stable isomers are contemplated in the present disclosure. Cis- and trans- (or E- and Z-) geometric isomers of the compounds of the present disclosure are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography, fractional crystallization, or through the use of a chiral agent. Depending on the process conditions the end products of the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric compounds of the present disclosure may be separated into the individual isomers. Compounds of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure. Further, a given chemical formula or name shall encompass all conformers, rotamers, or conformational isomers thereof where such isomers exist. Different conformations can have different energies, can usually interconvert, and are very rarely isolatable. There are some molecules that can be isolated in several conformations. For example, atropisomers are isomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

As used herein "metal-organic frameworks" or MOFs are compounds having a lattice structure made from (i) a cluster of metal ions as vertices ("cornerstones")("secondary building units" or SBUs) which are metal-based inorganic groups, for example metal oxides and/or hydroxides, linked together by (ii) organic linkers. The linkers are usually at least bidentate ligands which coordinate to the metal-based inorganic groups via functional groups such as carboxylates and/or amines. MOFs are considered coordination polymers made up of (i) the metal ion clusters and (ii) linker building blocks.

The term "isoreticular" as used herein is given its ordinary meaning, and thus refers to metal-organic frameworks (MOFs) which have the same network topology.

The term "chromate anions" as used herein, unless otherwise specified, refers to oxyanions of chromium in the 6+ oxidation state, and is meant to include monochromate anions ($CrO_4^{2-}$) as well as all polyoxyanions of chromium (VI) that may be formed from (poly)condensation of two or more monochromate anions, including dichromate anions ($Cr_2O_7^{2-}$), trichromate anions ($Cr_3O_{10}^{2-}$), tetrachromate anions ($Cr_4O_{13}^{2-}$), etc.

Metal-Organic Framework

The present disclosure provides a zirconium metal-organic framework (Zr-MOF) that may be used as a chemosensor for the sensitive and selective detection of copper cations and/or chromate anions in a fluid sample, including those fluid samples which contain a host of different cations/anions. The Zr-MOF disclosed herein is easy to manufacture, is stable under a wide range of pH, temperature, and solvent conditions, and when exposed to copper cations and/or chromate anions, produces a fluorescence emission peak of reduced intensity, but remains unchanged when in the presence of other common cations/anions. This characteristic allows for extremely easy detection and/or quantification of copper cations and/or chromate anions.

Generally, metal-organic frameworks (MOFs) are composed of two major components, (i) a cluster of metal ions in the form of inorganic oxides and/or hydroxides often called a "cornerstone" or "secondary building units" (SBUs) and (ii) an organic "linker" which coordinates to/connects two (or more) of the metal ion clusters to form a coordinated network. The structures may be one- two- or three-dimensional. As such, MOFS may often be referred to as hybrid organic-inorganic materials. The organic linkers are typically multivalent (e.g., di-, tri-, tetra-valent) ligands, and the choice of metal ion and linker dictates the structure and hence properties of the MOF. For example, the metal's coordination preference influences the size and shape of pores by dictating how many ligands can bind to the metal and in which orientation. MOFs usually contain pores (cages) which are present in the voids between the coordinated network of metal ion clusters and organic linker compounds. The pores are typically micropores having a diameter of 2 nm or less, preferably 1.5 nm or less, preferably 1 nm or less, or mesopores having a diameter of 2 to 50 nm, preferably 3 to 45 nm, preferably 4 to 40 nm, preferably 5 to 35 nm, preferably 6 to 30 nm.

The MOF of the present disclosure is preferably based on zirconium ions (made from zirconium ion clusters), referred to herein as a zirconium metal-organic framework (Zr-MOF). The Zr-MOF herein is intended to cover any MOF which contains predominantly zirconium ions with respect to the total metal ion content. The Zr-MOFs of the disclosure include zirconium ion clusters (cornerstones) which are zirconium inorganic groups, typically zirconium ions connected by bridging oxygen groups, bridging hydroxide groups, or both. These zirconium ion clusters are further coordinated to at least one linker. In some cases, the zirconium ion clusters may be further connected to non-bridging modulator species, complexing reagents or ligands (e.g. sulfates or carboxylates such as formate, benzoate, acetate, etc.) and/or solvent molecules (e.g., $H_2O$). The idealized zirconium ion cluster is considered to be a hexanuclear zirconium ion cluster based on an octahedron of zirconium ions ($Zr^{4+}$) which are $\mu_3$-bridged by $O^{2-}$ and/or $OH^-$ ions via the faces of the octahedron and further saturated by coordinating ligands containing oxygen atoms like carboxylate groups. Preferably, each zirconium ion cluster is coordinated by between 6 and 12 carboxylate groups, or between 8 and 11 carboxylate groups, or 10 carboxylate groups (preferentially as close as possible to 12 carboxylate groups), the carboxylate groups being from the linker and/or a modulator. However, in practice, there is a degree of flexibility in the structure of the zirconium ion cluster.

The zirconium ion cluster core structure herein (carboxylate ligands and overall charges not represented) may be of formula $[Zr_6O_x(OH)_{8-x}]$ wherein x is in the range 0 to 8, preferably 1 to 7, preferably 2 to 6, preferably 3 to 5, preferably 4. For example, the zirconium ion cluster core structure may be represented by the formula $[Zr_6O_4(OH)_4]$. In preferred embodiments, the zirconium ion clusters (with charges represented) are of formula $[Zr_6O_4(OH)_4]^{12+}$, which when coordinated to 12 carboxylate ligands (represented by "COO", originating from the linker and/or a modulator) in a coordination product, may be of formula $[Zr_6(\mu_3\text{-}O)_4(\mu_3\text{-}OH)_4(COO)_{12}]$. In Zr-MOFs which include zirconium ion clusters coordinated to fewer than 12 carboxylate ligands, each missing carboxylate ligand may be replaced by a pair of $OH^-/H_2O$ ligands to balance the charge. For example, zirconium ion clusters coordinated to 11-carboxylate ligands may be of formula $[Zr_6(\mu_3\text{-}O)_4(\mu_3\text{-}OH)_4(OH)(H_2O)(COO)_{11}]$, zirconium ion clusters coordinated to 10-carboxylate ligands may be of formula $[Zr_6(\mu_3\text{-}O)_4(\mu_3\text{-}OH)_4(OH)_2(H_2O)_2(COO)_{10}]$, zirconium ion clusters coordinated to 8-carboxylate ligands may be of formula $[Zr_6(\mu_3\text{-}O)_4(\mu_3\text{-}OH)_4(OH)_4(H_2O)_4(COO)_8]$, and zirconium ion clusters coordinated to 6-carboxylate ligands may be of formula $[Zr_6(\mu_3\text{-}O)_4(\mu_3\text{-}OH)_4(OH)_6(H_2O)_6(COO)_6]$.

The zirconium molecular organic frameworks of the present disclosure preferably contain greater than 50 wt. % of zirconium ions, preferably greater than 60 wt. % of zirconium ions, preferably greater than 70 wt. % of zirconium ions, preferably greater than 80 wt. % of zirconium ions, preferably greater than 85 wt. % of zirconium ions, preferably greater than 90 wt. % of zirconium ions, preferably greater than 95 wt. % of zirconium ions, preferably greater than 99 wt. % of zirconium ions, preferably 100 wt. % of zirconium ions, based on a total weight of metal ions present. If additional metal ions are present (other than zirconium ions) these may be present in an amount of less than 50 wt. %, preferably less than 40 wt. %, preferably less than 30 wt. %, preferably less than 20 wt. %, preferably less than 15 wt. %, preferably less than 10 wt. %, preferably less than 5 wt. %, preferably less than 1 wt. %, based on a total weight of metal ions. Additional metal ions may include, but are not limited to, ions of hafnium, titanium, and cerium. Such mixed metal MOFs may be prepared using methods known by those of ordinary skill in the art, including, but not limited to, post-synthetic metal exchanges.

In preferred embodiments, the zirconium metal-organic framework herein is isoreticular with metal-organic framework UiO-66. UiO-66 is an archetypal zirconium-based metal-organic framework that is constructed from hexanuclear zirconium oxide/hydroxide ion clusters as secondary building units (SBUs) and 1,4-benzenedicarboxylate (BDC) linkers. UiO-66 is constructed by linking 12-connected $[Zr_6(\mu_3\text{-}O)_4(\mu_3\text{-}OH)_4(COO)_{12}]$ clusters with linear BDC linkers into a network with face centered cubic (fcu) topology. UiO-66 possesses two types of micropores, tetrahedral (0.7 nm) and octahedral (0.9 nm), with a BET surface area of 1180 to 1240 $m^2/g$ and a pore volume of about 0.44 $cm^3/g$.

The Zr-MOF of the present disclosure is preferably of the UiO-66 type, having the same crystal structure and connectivity (topology) as UiO-66, differing only in the functionalization of the BDC-type linker used in the synthesis. Thus, the Zr-MOF of the present disclosure differs from UiO-66 by the presence of its functionalized framework, which as will become clear, effects its surface properties, reactivity, and ultimately its cation/anion sensing properties.

In addition to the zirconium ion clusters (cornerstones), the Zr-MOFs of the present disclosure are formed from at least one linker, which may be bidentate, tridentate, or tertadentate, and which links together adjacent zirconium ion clusters to form the coordinated network. In preferred embodiments, the linker is of formula (I)

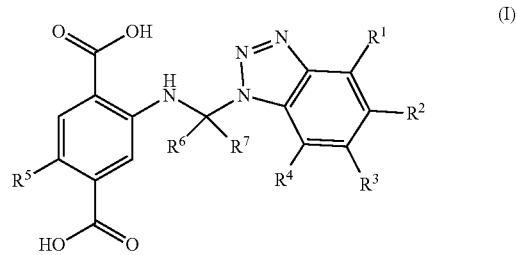

wherein:

R¹ to R⁴ are independently hydrogen, an optionally substituted alkyl, an optionally substituted aryl, an optionally substituted arylalkyl, an optionally substituted alkoxy, a hydroxyl, a carboxyl, a halo, a nitro, or a cyano, R⁵ is hydrogen, an optionally substituted alkyl, an optionally substituted alkoxy, an amino, a hydroxyl, a carboxyl, a halo, a nitro, or a cyano, and R⁶ and R⁷ are independently a hydrogen or an optionally substituted alkyl group having 1 to 4 carbon atoms.

In some embodiments, R¹ to R⁴ are independently hydrogen; an optionally substituted alkyl, preferably an optionally substituted $C_1$ to $C_6$ alkyl, preferably an optionally substituted $C_2$ to $C_5$ alkyl, preferably an optionally substituted $C_3$ to $C_4$ alkyl; an optionally substituted alkoxy, preferably an optionally substituted $C_1$ to $C_6$ alkoxy, preferably an optionally substituted $C_2$ to $C_5$ alkoxy, preferably an optionally substituted $C_3$ to $C_4$ alkoxy; a hydroxyl; a halo; preferably a chloro or bromo; a nitro; or a cyano. In preferred embodiments, R¹ to R⁴ are hydrogen.

In some embodiments, R⁵ is hydrogen; an optionally substituted alkyl, preferably an optionally substituted $C_1$ to $C_6$ alkyl, preferably an optionally substituted $C_2$ to $C_5$ alkyl, preferably an optionally substituted $C_3$ to $C_4$ alkyl; an optionally substituted alkoxy, preferably an optionally substituted $C_1$ to $C_6$ alkoxy, preferably an optionally substituted $C_2$ to $C_5$ alkoxy, preferably an optionally substituted $C_3$ to $C_4$ alkoxy; an amino, preferably a disubstituted amino, for example a dialkylamino such as dimethylamino or diethylamino; or a hydroxyl. In preferred embodiments, R⁵ is hydrogen.

R⁶ and R⁷ may be the same or different, preferably the same. In some embodiments, R⁶ and R⁷ are independently a hydrogen or an optionally substituted $C_1$ to $C_4$ alkyl group, preferably an preferably an optionally substituted $C_2$ to $C_3$ alkyl group. In preferred embodiments, R⁶ and R⁷ are hydrogen.

The zirconium metal-organic framework may have a zirconium ion to linker molecular ratio of 0.5:1 to 2:1, preferably 0.6:1 to 1.8:1, preferably 0.7:1 to 1.6:1, preferably 0.8:1 to 1.4:1, preferably 0.9:1 to 1.2:1, preferably 1:1.

The zirconium metal-organic framework may be constructed using a single linker or a mixture of two or more linkers. For example, a mixture of two or more linkers that fall within the general formula (I) may be used for make the Zr-MOF. Alternatively a mixture of two or more linkers may be used, whereby at least one linker falls within the general formula (I) and at least one linker that falls outside of general formula (I), for example 1,4-benzenedicarboxylate (BDC), 2-amino-1,4-benzenedicarboxylic acid (NH₂—BDC), 2-bromo-1,4-benzenedicarboxylic acid (Br-BDC), and 2-nitro-1,4-benzenedicarboxylic acid (NO₂—BDC), just to name a few. It is preferred, however, that the Zr-MOF of the present disclosure is the coordination product resulting from use a single linker.

In preferred embodiments, the linker is

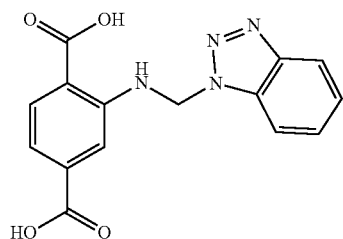 [SMILES: O=C(O)c1ccc(C(=O)O)c(NCn2nnc3ccccc32)c1]

(2-(((1H-benzo[d][1,2,3]triazol-1-yl)methyl)amino) terephthalic acid)

The linker of formula (I) may be synthesized or otherwise obtained by methods known to those of ordinary skill in the art. For example, the linker of formula (I) may be obtained according to the scheme outlined in FIG. 11.

Briefly, an amine of formula (II) and a benzotriazole of formula (III) may be cross-condensed with a carbonyl compound of formula (IV)

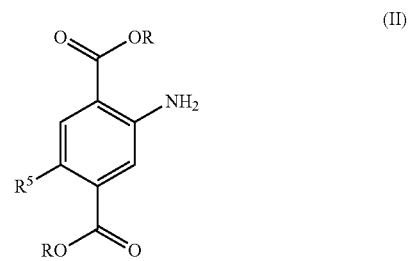

(II)

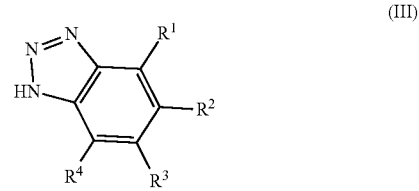

(III)

(IV)

wherein R¹, R², R³, R⁴, R⁵, R⁶, and R⁷ are as defined previously, and R is an optionally substituted alkyl (e.g., methyl, ethyl, etc.), and optionally substituted aryl (e.g., phenyl), an optionally substituted arylalkyl (e.g., benzyl, p-methoxybenzyl, etc.), or any other group that is known to form an ester protecting group that may be subsequently cleaved to provide a carboxylic acid. Preferably R is an optionally substituted alkyl group, preferably methyl or ethyl.

The cross-condensation reaction may be performed using any procedures known to those of ordinary skill in the art, including, but not limited to, room temperature conditions, high temperature/organic solvent conditions, and microwave conditions, optionally in the presence of a catalyst (e.g., para-toluene sulfonic acid, ammonium acetate, HCl, $H_2SO_4$, polyphosphoric acid, boron trifluoride, zinc chloride, iron chloride, aluminum chloride, etc.). Preferably, the condensation reaction is performed by stirring the compounds of formulae (II and III) in an alcoholic solvent (e.g., methanol, ethanol, propanol, isopropanol, etc.), in the presence of the carbonyl compound of formula (IV), which may be for example, formaldehyde, acetaldehyde, propionaldehyde, butyraldehyde, acetone, methyl ethyl ketone, etc., to produce an aminal compound of formula (V)

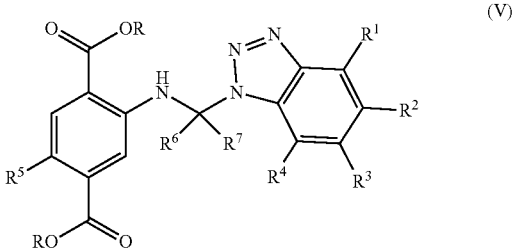

(V)

wherein $R^1$, $R^2$, $R^3$, $R^4$, $R^5$, $R^6$, $R^7$, and R are as defined previously.

Cleavage of the R group from the aminal compound of formula (V) under suitable conditions may then form the linker of formula (I). Conditions suitable for the cleavage of the R group depend on the nature of R (and the other substituents present). For example, when R is an alkyl group having 1 to 3 carbon atoms, cleavage of R may be performed under standard saponification conditions such as using water, an alcohol (e.g., ethanol), and a hydroxide or carbonate base (e.g., KOH).

Owing at least in part to the sterically bulky benzotriazole functionality on the 1,4-benzenedicarboxylic core, which without being bound by theory may act to partially obstruct the pores of the MOF structure, the Zr-MOF herein may have a BET surface area of 300 to 600 m$^2$/g, preferably 310 to 600 m$^2$/g, preferably 320 to 550 m$^2$/g, preferably 330 to 500 m$^2$/g, preferably 340 to 450 m$^2$/g, preferably 350 to 400 m$^2$/g, preferably 360 to 395 m$^2$/g, preferably 370 to 390 m$^2$/g, preferably 380 to 386 m$^2$/g, preferably 384 m$^2$/g. Further, the Zr-MOF may have a pore volume of 0.2 to 0.4 cm$^3$/g, preferably 0.21 to 0.38 cm$^3$/g, preferably 0.22 to 0.36 cm$^3$/g, preferably 0.23 to 0.34 cm$^3$/g, preferably 0.24 to 0.32 cm$^3$/g, preferably 0.25 to 0.3 cm$^3$/g, preferably 0.26 to 0.29 cm$^3$/g, preferably 0.27 to 0.28 cm$^3$/g, preferably 0.275 cm$^3$/g. Both the surface are and pore volume values of the Zr-MOF of the present disclosure are thus significantly smaller compared to those reported for UiO-66 (BET surface area of 1180 to 1240 m$^2$/g and a pore volume of about 0.44 cm$^3$/g) as well as functionalized variants such as UiO-66-NH$_2$ (prepared using 2-amino-1,4-benzenedicarboxylic acid (NH$_2$—BDC) linkers, BET surface area of 1067 m$^2$/g and a pore volume of 0.517 cm$^3$/g).

In some embodiments, the zirconium metal-organic framework of the present disclosure has a particle size of 0.1 to 1 µm, preferably 0.12 to 0.9 µm, preferably 0.14 to 0.8 µm, preferably 0.16 to 0.7 µm, preferably 0.18 to 0.6 µm, preferably 0.2 to 0.5 µm, preferably 0.3 to 0.4 µm, and each particle may have clearly visible facets.

One of the advantages of the UiO-66 network is it's remarkable thermal stability. Use of the linker of formula (I) has been found not to negatively impact the thermal stability of the Zr-MOF compared to UiO-66. In some embodiments, the Zr-MOF herein is thermally stable up to 410° C.

The zirconium metal-organic framework obtained from coordination between zirconium ion clusters and the linker of formula (I) may have a fluorescence emissions peak at 480 to 500 nm, preferably 482 to 498 nm, preferably 484 to 496 nm, preferably 486 to 494 nm, preferably 488 to 492 nm, preferably 491 nm, when excited at an excitation wavelength of 360 nm. Such a fluorescence emissions peak (maximum) is red shifted by 31 to 51 nm, preferably 33 to 49 nm, preferably 35 to 47 nm, preferably 37 to 45 nm, preferably 39 to 43 nm, preferably 42 nm compared to the fluorescence emissions peak of UiO-66-NH$_2$.

It has been surprisingly found that the zirconium metal-organic framework of the present disclosure is extremely sensitive for the detection of copper cations and/or chromate anions in various fluids, and is advantageously selective towards copper cations and/or chromate anions even when other ions are present in abundance. That is, the Zr-MOF herein produces a strong fluorescence emission in the absence of copper cations and/or chromate anions (and optionally in the presence of various other cations such as cobalt, iron, nickel, palladium, sodium, lead, cadmium, mercury, zinc, potassium, calcium, magnesium, strontium, rubidium, cesium, silver, aluminum, and gallium and/or anions such as fluoride, acetate, phosphate, chloride, bromide, iodide, sulfate, bisulfate, permanganate, and nitrate), but upon interaction with copper cations and/or chromate anions, the fluorescence emission intensity is quenched as a function of the copper cation and/or chromate anion concentration. Therefore, the presence/absence of copper cations/chromate anions, as well as the concentration of these ions in the fluid sample, can be determined based on the reduction/degree of reduction of the intensity of the fluorescence emissions peak.

A Method of Making the Zirconium Metal-Organic Framework

The present disclosure also provides methods for making the zirconium metal-organic frameworks. Preferably, pre-synthetic modification methods are utilized to construct the MOF structure using prefunctionalized linkers (e.g., of formula (I)). While any synthetic techniques may be utilized, in preferred embodiments, the Zr-MOFs herein are prepared using solvothermal synthesis techniques to form a coordination product between zirconium ion clusters and the linker of formula (I).

The methods herein may first involve mixing together a zirconium(IV) salt and the linker of formula (I) in a polar aprotic solvent to form a complexation mixture. A concentration of the zirconium(IV) salt in the complexation mixture may range from 0.02 to 0.04 M, preferably 0.022 to 0.036 M, preferably 0.024 to 0.032 M, preferably 0.026 to 0.03 M, preferably 0.027 M. The zirconium(IV) salt may include, but is not limited to, zirconium(IV) chloride, zirconium(IV) bromide, zirconium(IV) acetylacetonate, zirconium(IV) fluoride, zirconium(IV) hydroxide, zirconium(IV) acetate hydroxide, and zirconium(IV) trifluoroacetylacetonate, preferably zirconium(IV) chloride.

In some embodiments, a concentration of the linker of formula (I) in the complexation mixture is 0.025 to 0.045 M, preferably, 0.03 to 0.043 M, preferably 0.032 to 0.041 M, preferably 0.034 to 0.040 M, preferably 0.036 to 0.039 M, preferably 0.037 to 0.038 M. In some embodiments, a molar ratio of the linker of formula (I) to the zirconium(IV) salt in the complexation mixture is from 1:1 to 2:1, preferably 1.1:1 to 1.8:1, preferably 1.2:1 to 1.6:1, preferably 1.3:1 to 1.4:1, preferably 1.35:1 to 1.39:1.

The polar aprotic solvent may include, but is not limited to, dimethylformamide (DMF), N-methyl-2-pyrrolidone, dimethyl sulfoxide, acetone, acetonitrile, dimethylacetamide, and 1,3-dimethyl-2-imidazolidinone, preferably dimethylformamide.

The zirconium(IV) salt, the linker of formula (I), and the polar aprotic solvent may be mixed by any suitable technique for any period of time until complete dissolution is achieved. For example, the ingredients may be stirred, shaken, ultrasonicated, or otherwise agitated for 1 to 60 minutes, preferably 5 to 50 minutes, preferably 10 to 45 minutes, preferably 20 to 40 minutes, preferably 30 to 35 minutes. In preferred embodiments, the ingredients are ultrasonically mixed to form the complexation mixture.

After forming the complexation mixture, a modulator may next be added to form a modulated mixture. Any amount of modulator may be used which still allows the linker of formula (I) to form the desired coordinated network topology (e.g., isoreticular with respect to UiO-66), typically a volume ratio of the polar aprotic solvent to the modulator in the modulated mixture is from 20:1 to 60:1, preferably 25:1 to 55:1, preferably 30:1 to 50:1, preferably 35:1 to 45:1, preferably 40:1. The modulator used herein may include, but is not limited to, acetic acid, formic acid, benzoic acid, trifluoroacetic acid, and hydrochloric acid, preferably acetic acid is employed as the modulator.

Next, the modulated mixture may be heated, for example heated under solvothermal conditions in an acceptable vial, vessel, or autoclave to a temperature of 100 to 150° C., preferably 105 to 145° C., preferably 110 to 140° C., preferably 115 to 135° C., preferably 120 to 130° C., for 12 to 72 hours, preferably 16 to 48 hours, preferably 20 to 36 hours, preferably 24 to 30 hours. Under such coordination conditions, the Zr-MOF of the present disclosure may be formed by self-assembly of the building blocks (i.e., zirconium ion clusters and the linker of formula (I)) and may precipitate from solution due to insolubility in the reaction environment. It is preferred that the Zr-MOF herein is formed by self-assembly, and thus the methods of the present disclosure do not require the use of surfactants, structure-directing agents, complexing agents, or templating agents.

Once formed, the Zr-MOF may be separated from the modulated mixture using any known solid-liquid separation technique (e.g., filtration, decantation, centrifugation, etc.) and optionally washed with a polar aprotic solvent (e.g., DMF). In preferred embodiments, the collected Zr-MOF is washed with DMF, preferably washed with DMF at least 2 times, preferably at least 3 times, with centrifugation at 5,000 to 15,000 rpm, preferably at 10,000 rpm following each washing iteration. After washing with the polar aprotic solvent, the Zr-MOF may optionally be immersed in an alcohol (e.g., methanol), for example immersed in an alcohol at least 2 times per day, preferably at least 3 times per day, and the immersion may be performed for 1 day, preferably for 2 consecutive days, preferably for 3 consecutive days, most preferably immersed in methanol 3 times per day for 3 consecutive days.

Lastly, it is preferred to dry the Zr-MOF under vacuum and at elevated temperature, for example, at 70 to 130° C., preferably 80 to 120° C., preferably 90 to 110° C., preferably 100° C., in order to remove any solvent molecules that may remain in the octahedral and/or tetrahedral pores (cages) prior to use.

A Method of Detecting Copper Cations and/or Chromate Anions

The present disclosure also provides a method of detecting copper cations and/or chromate anions in a fluid sample that involves contacting the fluid sample with the zirconium metal-organic framework to form a mixture, and measuring a fluorescence emission profile of the mixture to determine whether copper cations and/or chromate anions are present in the fluid sample and/or to quantify the amount of copper cations and/or chromate anions present in the fluid sample, based on the intensity of the fluorescence emissions peak at 480 to 500 nm as discussed above.

Fluid Sample

The fluid sample that may be analyzed by the methods of the present disclosure is not particularly limited, and may be aqueous, an oil-in-water mixture, or a mixed aqueous and organic solvent mixture. The fluid sample may be obtained from any source that may contain or is suspected of containing copper cations and/or chromate anions. In some embodiments, the fluid sample is obtained from a natural water source (lakes, rivers, oceans, aquifers, etc.) or purified water sources (e.g., potable drinking water). In some embodiments, the fluid sample is a wastewater, particularly an industrial wastewater, for example, wastewater produced in/during automotive manufacturing processes, semiconductor manufacturing processes, cable manufacturing operations, battery manufacturing operations, metallurgy, welding, alloying, and steel production, medicinal and chemical production plants, electroplating facilities, pigment production plants, leather tanning facilities, detergent manufacturing plants, and wood preservation facilities, etc.

In some embodiments, the fluid sample is aqueous, and is substantially free of both oil and organic solvent. The aqueous fluid may be fresh water (e.g., water obtained from streams, rivers, lakes, ground water, aquifers, purified water, tap water, well water, wastewater having low salinity such as wastewater deposited into fresh water sources, etc.) or salt water (e.g., seawater, coastal aquifers, or wastewater having high salinity).

In some embodiments, the fluid sample is an oil-in-water mixture, and may contain up to 10%, preferably up to 8%, preferably up to 6%, preferably up to 4%, preferably up to 2%, preferably up to 1% by volume of an oil, based on a total volume of the fluid sample. The oil may include a natural oil, a synthetic oil, or both. Examples of oils from natural sources include, but are not limited to, kerosene, diesel oils, crude oils, gas oils, fuel oils, paraffin oils, mineral oils, low toxicity mineral oils, other petroleum distillates, and any combination thereof. Examples of synthetic oils include, but are not limited to, polyolefins, polydiorganosiloxanes, siloxanes, organosiloxanes, as well as mixtures thereof.

In some embodiments, the fluid sample is a mixed aqueous and organic solvent mixture. The organic solvent that may be optionally present in the fluid sample is not particularly limited, and may include organic solvent(s) employed during various industrial processes that produce a wastewater that may contain or is suspected of containing copper cations and/or chromate anions, for example, the manufacturing operations described above. The organic solvent may be miscible or immiscible with water. Exemplary organic solvents that may be present in the fluid sample include, but is not limited to, aromatic solvents (e.g., benzene, ethylbenzene, o-xylene, m-xylene, p-xylene, and mixtures of xylenes, toluene, mesitylene, anisole, 1,2-dimethoxybenzene, $\alpha,\alpha,\alpha$,-trifluoromethylbenzene, fluorobenzene, heavy aromatic naptha), alkane solvents (e.g., pentane, cyclopentane, hexanes, cyclohexane, heptanes, cycloheptane, octanes), ethers (e.g. diethyl ether, tetrahydrofuran, 1,4-dioxane, tetrahydropyran, t-butyl methyl ether, cyclopentyl methyl ether, di-isopropyl ether), glycol ethers (e.g. 1,2-dimethoxyethane, diglyme, triglyme), chlorinated solvents (e.g. chlorobenzene, dichloromethane, 1,2-dichloroethane, 1,1-dichloroethane, chloroform, carbon tetrachloride), ester solvents (e.g. ethyl acetate, propyl acetate), ketones (e.g. acetone, butanone), formamides/acetamides (e.g., formamide, dimethyl formamide, dimethyl acetamide), monoalcohols (e.g., methanol, ethanol, propanol, isopropanol, n-butanol, isobutanol, n-pentanol, n-hexanol, terpineol, menthol, prenol, 3-methyl-3-buten-1-ol, 2-ethyl-1-hexanol, 2-ethyl-1-butanol, 2-propylheptan-1-ol, 2-butyl-1-octanol, benzyl alcohol), polyalcohols including glycols (e.g., ethylene glycol, diethylene glycol, triethylene glycol, tetraethylene glycol, propylene glycol, dipropylene glycol, 1,3-propanediol, 1,3-butanediol, 1,4-butanediol, 1,6-hexanediol, glycerol, pentaerythritol, manitol, sorbitol), as well as mixtures thereof. The fluid sample may contain up to 30%, preferably up to 25%, preferably up to 20%, preferably up to 15%, preferably up to 10%, preferably up to 5%, preferably up to 2%, preferably up to 1% by volume of an organic solvent(s) based on a total volume of the fluid sample. Typically, when an organic solvent is present in the fluid sample, a ratio of water to the organic solvent ranges from 5:1 to 100:1, preferably 6:1 to 75:1, preferably 7:1 to 50:1, preferably 8:1 to 25:1, preferably 9:1 to 15:1.

In addition to optionally containing an oil(s) and/or an organic solvent(s) as described above, the fluid sample may optionally contain suspended solids. In some embodiments, the fluid sample contains greater than 55% v/v of water, preferably greater than 60% v/v of water, preferably greater than 65% v/v of water, preferably greater than 70% v/v of water, preferably greater than 75% v/v of water, preferably greater than 80% v/v of water, preferably greater than 85% v/v of water, preferably greater than 90% v/v of water, preferably greater than 95% v/v of water, preferably greater than 99% v/v of water, based on a total volume of the fluid sample.

The fluid sample may contain copper cations (e.g., $Cu^{2+}$) and/or chromate anions (e.g., $CrO_4^{2-}$ and/or $Cr_2O_7^{2-}$). When present, the copper cations and/or chromate anions may be present in the fluid sample at a concentration of, for example, $1\times10^{-6}$ to $5\times10^{-1}$ M, preferably $2.5\times10^{-6}$ to $1\times10^{-1}$ M, preferably $5\times10^{-6}$ to $7.5\times10^{-2}$ M, preferably $7.5\times10^{-6}$ to $5\times10^{-2}$ M, preferably $1\times10^{-5}$ to $2.5\times10^{-2}$ M, preferably $2.5\times10^{-5}$ to $1\times10^{-2}$M, preferably $5\times10^{-5}$ to $7.5\times10^{-3}$M, preferably $7.5\times10^{-5}$ to $5\times10^{-3}$ M, preferably $1\times10^{-4}$ to $2.5\times10^{-3}$M, preferably $2.5\times10^{-4}$ to $1\times10^{-3}$ M, preferably $5\times10^{-4}$ to $7.5\times10^{-4}$ M. Examples of copper species that may be present in the fluid sample, which are in the form of copper cations (e.g., $Cu^{2+}$) or are capable of forming copper cations in situ include, but are not limited to, copper(II) sulfate, copper(II) nitrate, copper(II) oxide, copper(II) hydroxide, copper(II) carbonate, copper(II) chloride, copper(II) acetate, copper(II) bromide, copper(II) trifluoromethanesulfonate, copper(II) fluoride, copper(II) sulfide, copper(II) acetylacetonate, copper(II) tetrafluoroborate, copper(II) phthalocyanine, and copper(II) perchlorate, just to name a few. Examples of chromate species that may be present in the fluid sample, which are in the form of chromate anions (e.g., $CrO_4^{2-}$ and/or $Cr_2O_7^{2-}$) or are capable of forming chromate anions in situ include, but are not limited to, sodium chromate, ammonium chromate, potassium chromate, barium chromate, silver(I) chromate, calcium chromate, lead(II) chromate, magnesium chromate, pyridinium chromate, sodium dichromate, ammonium dichromate, potassium dichromate, and pyridinium dichromate just to name a few.

The fluid sample may also optionally include one or more other (non-copper) cations, including heavy and transitional metal cations as well as alkali and alkaline earth metal cations, such as cations of sodium, potassium, calcium, magnesium, barium, strontium, rubidium, cesium, iron (ferrous and ferric), arsenic, cobalt, copper, manganese, nickel, zinc, cadmium, mercury, silver, palladium, aluminum, gallium, chromium, and lead, including mixtures thereof. Representative examples of other (non-chromate) anions which may also be present in the fluid sample include, but are not limited to, chloride, carbonate, bicarbonate, sulfate, bromide, iodide, acetate, hydroxide, sulfide, hydrosulfide, chlorate, fluoride, hypochlorite, nitrate, nitrite, perchlorate, peroxide, phosphate, phosphite, sulfite, hydrogen phosphate, hydrogen sulfate (bisulfate), and permanganate, as well as mixtures thereof.

In some embodiments, monovalent cations (e.g., sodium ions, potassium ions, rubidium ions, cesium ions, silver(I) ions) may be present in the fluid sample in amounts of at least 5 ppm, preferably at least 10 ppm, preferably at least 20 ppm, preferably at least 30 ppm, preferably at least 40 ppm, preferably at least 50 ppm, and up to 100,000 ppm, preferably up to 75,000 ppm, preferably up to 50,000 ppm, preferably up to 40,000 ppm, preferably up to 30,000 ppm, preferably up to 20,000 ppm, preferably up to 15,000 ppm, preferably up to 10,000 ppm, preferably up to 5,000 ppm, preferably up to 1,000 ppm, preferably up to 500 ppm, preferably up to 100 ppm.

The fluid sample may also generally contain up to 50,000 ppm of multivalent (non-copper(II)) cations (e.g., magnesium ions, calcium ions, iron ions, strontium ions, barium ions, lead ions, cobalt ions, cadmium ions, mercury ions, manganese ions, nickel ions, zinc ions, arsenic ions, chromium ions, palladium ions, gallium ions, and/or aluminum ions, etc.), for example at least 5 ppm, preferably at least 10 ppm, preferably at least 20 ppm, preferably at least 30 ppm, preferably at least 40 ppm, preferably at least 50 ppm, preferably at least 75 ppm, preferably at least 100 ppm, preferably at least 150 ppm, preferably at least 200 ppm, preferably at least 500 ppm, preferably at least 1,000 ppm, preferably at least 2,000 ppm, preferably at least 5,000 ppm, and up to 50,000 ppm, preferably up to 40,000 ppm, preferably up to 30,000 ppm, preferably up to 20,000 ppm, preferably up to 10,000 ppm, preferably up to 7,000 ppm, preferably up to 6,000 ppm total of multivalent cations.

In some embodiments, the fluid sample has a total dissolved solids (TDS) content of up to 200,000 ppm, for example 100 to 200,000 ppm, preferably 500 to 180,000 ppm, preferably 1,000 to 150,000 ppm, preferably 1,500 to 100,000 ppm, preferably 2,000 to 80,000 ppm, preferably 3,000 to 60,000 ppm, preferably 4,000 to 40,000 ppm, preferably 5,000 to 20,000 ppm, preferably 6,000 to 10,000 ppm.

The fluid sample (and thus the mixture) may contain a surfactant. Alternatively, prior to the contacting, a surfactant may be added to the fluid sample, for example, when the fluid sample to be tested is an oil-in-water mixture (e.g., a wastewater) to better disperse/distribute the Zr-MOF throughout the fluid sample. The surfactant may be a cationic, anionic, non-ionic, and/or amphoteric surfactant, and may be present in the fluid sample in an amount of up to 5 wt. %, preferably up to 4 wt. %, preferably up to 3 wt. %, preferably up to 2 wt. %, preferably up to 1 wt. %, preferably up to 0.5 wt. %, preferably up to 0.1 wt. %, based on a total weight of the fluid sample.

Cationic surfactants may include, but are not limited to
a protonated amine formed from a reaction between a $C_6$-$C_{26}$ alkyl amine compound and an acid (e.g., acetic acid, formic acid, propionic acid, butyric acid, pentanoic acid, hexanoic acid, oxalic acid, malonic acid, lactic acid, glyceric acid, glycolic acid, malic acid, citric acid, benzoic acid, p-toluenesulfonic acid, trifluoromethanesulfonic acid, hydrochloric acid, nitric acid, phosphoric acid, sulfuric acid, hydrobromic acid, perchloric acid, hydroiodic acid, etc.), such as protonated salts of $C_6$-$C_{26}$ alkyl monoamines, $C_6$-$C_{26}$ alkyl (poly)alkylene polyamines, and alkoxylated fatty amines;

a protonated $C_6$-$C_{26}$ alkyl amidoamine formed from a reaction between a $C_6$-$C_{26}$ alkyl amidoamine compound and an acid (for example the acids listed above), such as protonated forms of the amide reaction product between any fatty acid previously listed (or ester derivative thereof) with a polyamine (e.g., putrescine, cadaverine, ethylene diamine, $N^1,N^1$-dimethylethane-1,2-diamine, $N^1,N^1$-dimethylpropane-1,3-diamine, $N^1,N^1$-diethylethane-1,2-diamine, $N^1,N^1$-diethylpropane-1,3-diamine, spermidine, 1,1,1-tris(aminomethyl) ethane, tris(2-aminoethyl)amine, spermine, TEPA, DETA, TETA, AEEA, PEHA, HEHA, dipropylene triamine, tripropylene tetramine, tetrapropylene pentamine, pentapropylene hexamine, hexapropylene heptamine, dibutylene triamine, tributylene tetramine, tetrabutylene pentamine, pentabutylene hexamine, hexabutylene heptamine), with specific mention being made to protonated forms of stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylmine, behenamidoethyldiethylamine, behenamidoethyldimethylamine, arachidamidopropyldimethylamine, arachidamidopropyldiethylamine, arachidamidoethyldiethylamine, and arachidamidoethyldimethylamine; and a quaternary ammonium compound made from alkylation with suitable alkylating agents (e.g., dimethyl sulfate, methyl chloride or bromide, benzyl chloride or bromide, $C_6$-$C_{26}$ alkyl chloride or bromide, etc.) of a tertiary $C_6$-$C_{26}$ alkyl amine, an alkoxylated (tertiary) amine, or an aprotic nitrogenous heteroarene (optionally substituted) having at least one aromatic nitrogen atom with a reactive lone pair of electrons, with specific mention being made to a tri-fatty alkyl lower alkyl ammonium compound (e.g., trioctyl methyl ammonium chloride), a $C_{10}$-$C_{18}$ alkyl trimethyl ammonium chloride or methosulfate, a di-$C_{10}$-$C_{18}$ alkyl dimethyl ammonium chloride or methosulfate, a $C_{10}$-$C_{18}$ alkyl benzyl dimethyl ammonium chloride, a methyl quaternized $C_6$-$C_{22}$ alkyl propylene diamine, a methyl quaternized $C_6$-$C_{22}$ alkyl propylene triamine, a methyl quaternized $C_6$-$C_{22}$ alkyl propylene tetraamine, a N—$C_{10}$-$C_{18}$ alkyl pyridinium or a quinolinium bromide or chloride such as N-octyl pyridinium bromide, N-nonyl pyridinium bromide, N-decyl pyridinium bromide, N-dodecyl pyridinium bromide, N-tetradecyl pyridinium bromide, N-dodecyl pyridinium chloride, N-cyclohexyl pyridinium bromide, naphthyl methyl quinolinium chloride, naphthyl methyl pyridinium chloride, and cetylpyridinium chloride (for example those disclosed in CN101544903B—incorporated herein by reference in its entirety);

as well as mixtures thereof.

Anionic surfactants may include, but are not limited to:

sulfates, such as alkyl sulfates, alkyl-ester-sulfates, alkyl ether sulfates, alkyl-alkoxy-ester-sulfate, sulfated alkanolamides, glyceride sulfates, in particular, sulfates of fatty alcohols or polyoxyalkylene ethers of fatty alcohols such as sodium dodecyl sulfate, sodium laureth sulfate, ammonium lauryl sulfate, potassium lauryl sulfate, sodium myreth sulfate;

sulfonates such as alkyl sulfonates, fatty alkyl-benzene sulfonates, lower alkyl-benzene sulfonates, alpha olefin sulfonates, lignosulfonates, sulfo-carboxylic compounds, for example, dodecyl benzene sulfonate, dioctyl sodium sulfosuccinate, perfluorooctanesulfonate (PFOS), perfluorobutanesulfonate;

phosphates such as alkyl aryl ether phosphates, alkyl ether phosphates, phosphates of fatty alcohols or polyoxyalkylene ethers of fatty alcohols such as cetyl phosphate salts, dicetyl phosphate salts, ceteth-10-phosphate salts;

carboxylate salts of fatty acids, acylamino acids, lactylates, and/or fatty alcohols/polyoxyalkylene ethers of fatty alcohols such as sodium stearate, vegetable oil-based anionic surfactants (e.g., palm oil anionic surfactant), sodium behenoyl lactylate, sodium isostearoyl lactylate, sodium caproyl lactylate, sodium laureth-5 carboxylate, sodium laureth-6 carboxylate, sodium laureth-11 carboxylate;

and mixtures thereof.

Non-ionic surfactants may include, but are not limited to:

amides or alkanolamides of fatty acids, that is, amide reaction products between a fatty acid and an amine or alkanolamine compound, such as coconut fatty acid monoethanolamide (e.g., N-methyl coco fatty ethanol amide), coconut fatty acid diethanolamide, oleic acid diethanolamide, palm based oleylamine, and vegetable oil fatty acid diethanolamide;

alkoxylated alkanolamides of fatty acids, preferably ethoxylated and/or propoxylated variants of the alkanolamides of fatty acids using for example anywhere from 2 to 30 EO and/or PO molar equivalents, preferably 3 to 15 EO and/or PO molar equivalents, preferably 4 to 10 EO and/or PO molar equivalents, preferably 5 to 8 EO and/or PO molar equivalents per moles of the alkanolamide of the fatty acid (e.g., coconut fatty acid monoethanolamide with 4 moles of ethylene oxide);

amine oxides, such as N-cocoamidopropyl dimethyl amine oxide and dimethyl $C_6$-$C_{22}$ alkyl amine oxide (e.g., dimethyl coco amine oxide);

fatty esters, such as ethoxylated and/or propoxylated fatty acids (e.g., castor oil with 2 to 40 moles of ethylene oxide), alkoxylated glycerides (e.g., PEG-24 glyceryl monostearate), glycol esters and derivatives, monoglycerides, polyglyceryl esters, esters of polyalcohols, and sorbitan/sorbitol esters;

ethers, such as (i) alkoxylated $C_1$-$C_{22}$ alkanols, which may include alkoxylated $C_1$-$C_5$ alkanols, preferably ethoxylated or propoxylated $C_1$-$C_5$ alkanols (e.g., dipropylene glycol n-butyl ether, tripropylene glycol n-butyl ether, dipropylene glycol methyl ether, tripropylene glycol methyl ether, diethylene glycol n-butyl ether, triethylene glycol n-butyl ether, diethylene glycol methyl ether, triethylene glycol methyl ether) and alkoxylated $C_6$-$C_{26}$ alkanols (including alkoxylated fatty alcohols), preferably alkoxylated $C_7$-$C_{22}$ alkanols, more preferably alkoxylated $C_{14}$ alkanols, preferably ethoxylated or propoxylated (e.g., cetyl stearyl alcohol with 2 to 40 moles of ethylene oxide, lauric alcohol with 2 to 40 moles of ethylene oxide, oleic alcohol with 2 to 40 moles of ethylene oxide, ethoxylated lanoline derivatives, laureth-3, ceteareth-6, ceteareth-11, ceteareth-15, ceteareth-16, ceteareth-17, ceteareth-18, ceteareth-20, ceteareth-23, ceteareth-25, ceteareth-27, ceteareth-28, ceteareth-30, isoceteth-20, laureth-9/myreth-9, and PPG-3 caprylyl ether); (ii) alkoxylated polysiloxanes; (iii) ethylene oxide/propylene oxide copolymers (e.g., PPG-1-PEG-9-lauryl glycol ether, PPG-12-buteth-16, PPG-3-buteth-5, PPG-5-buteth-7, PPG-7-buteth-10, PPG-9-buteth-12, PPG-12-buteth- 16, PPG-15-buteth-20, PPG-20-buteth-30, PPG-28-buteth-35, and PPG-33-buteth-45); and (iv) alkoxylated alkylphenols;

alkyl polyglycosides (APGs) such as those made from reaction between fatty alcohols and glucose;

and mixtures thereof.

Amphoteric surfactants may include, but are not limited to:

$C_6$-$C_{22}$ alkyl dialkyl betaines, such as fatty dimethyl betaines (R—N(CH$_3$)$_2$($^+$)—CH$_2$COO$^-$), obtained from a $C_6$-$C_{22}$ alkyl dimethyl amine which is reacted with a monohaloacetate salt (e.g., sodium monochloroacetate), such as $C_{12}$-$C_{14}$ dimethyl betaine (carboxylate methyl $C_{12}$-$C_{14}$ alkyl dimethylammonium);

$C_6$-$C_{22}$ alkyl amido betaines (R—CO—NH—CH$_2$CH$_2$CH$_2$—N(CH$_3$)$_2$($^+$)—CH$_2$COO$^-$ or R—CO—NH—CH$_2$CH$_2$—N(CH$_3$)$_2$($^+$)—CH$_2$COO$^-$), obtained by the reaction of a monohaloacetate salt (e.g., sodium monochloroacetate) with the reaction product of either dimethyl amino propylamine or dimethyl amino ethylamine with a suitable carboxylic acid or ester derivatives thereof, such as $C_{10}$-$C_{18}$ amidopropyl dimethylamino betaine;

$C_6$-$C_{22}$ alkyl sultaines or $C_6$-$C_{22}$ alkyl amido sultaines, which are similar to those $C_6$-$C_{22}$ alkyl dialkyl betaines or $C_6$-$C_{22}$ alkyl amido betaines described above except in which the carboxylic group has been substituted by a sulfonic group (R—N(CH$_3$)$_2$($^+$)—CH$_2$CH$_2$CH$_2$SO$_3^-$ or R—CO—NH—CH$_2$CH$_2$CH$_2$—N(CH$_3$)$_2$($^+$)—CH$_2$CH$_2$CH$_2$SO$_3^-$ or R—CO—NH—CH$_2$CH$_2$—N(CH$_3$)$_2$($^+$)—CH$_2$CH$_2$CH$_2$SO$_3^-$) or a hydroxysulfonic group (R—N(CH$_3$)$_2$($^+$)—CH$_2$CH(OH)—CH$_2$SO$_3^-$ or R—CO—NH—CH$_2$CH$_2$CH$_2$—N(CH$_3$)$_2$($^+$)—CH$_2$CH(OH)—CH$_2$SO$_3^-$ or R—CO—NH—CH$_2$CH$_2$—N(CH$_3$)$_2$($^+$)—CH$_2$CH(OH)—CH$_2$SO$_3$), such as $C_{10}$-$C_{18}$ dimethyl hydroxysultaine and $C_{10}$-$C_{18}$ amido propyl dimethylamino hydroxysultaine;

and mixtures thereof.

Contacting

The fluid sample may be contacted with the Zr-MOF to form the mixture using any method known to those of ordinary skill in the art. For example, the fluid sample may be added to Zr-MOF or the Zr-MOF may be added to the fluid sample. The Zr-MOF may be in the form of a solid or may be formed into a solution prior to the contacting. After combining the fluid sample with the Zr-MOF, the methods herein may involve manual stirring, mechanical stirring, shaking, blending, mixing, swirling, circulation techniques, sonication (e.g., ultrasonication), or any other agitation technique to form a mixture, preferably a homogenous mixture.

Any amount of the Zr-MOF may be contacted with the fluid sample that provides a reproducible and accurate fluorescence emissions readout. Typically, the Zr-MOF is employed in an amount of 0.001 to 10 mg, preferably 0.005 to 9 mg, preferably 0.01 to 8 mg, preferably 0.05 to 7 mg, preferably 0.1 to 6 mg, preferably 0.2 to 5 mg, preferably 0.3 to 4 mg, preferably 0.4 to 3 mg, preferably 0.5 to 2 mg, preferably 0.8 to 1 mg, per 1 mL of the fluid sample. Preferably, the Zr-MOF is the only copper cation/chromate anion-specific chemosensor present in the mixture. Preferably, the Zr-MOF is the only chemosensor present in the mixture.

In some embodiments, the fluid sample is added to the Zr-MOF as a single portion, or vice versa. Alternatively, the fluid sample may be added dropwise or portion wise (e.g., titrated) into the Zr-MOF with concomitant agitation, whereby the fluorescence emission profile of the mixture is optionally measured subsequent to each drop/portion of the fluid sample added. Such a procedure may be employed, for example, when it is desired to determine a concentration of copper cations and/or chromate anions in the fluid sample by generating a titration curve.

The methods herein enable ultra-fast detection of copper cations and/or chromate anions in a fluid sample, and extremely short contacting times may be used. In some embodiments, the Zr-MOF is contacted with the fluid sample for 1 second to 15 minutes, preferably 5 seconds to 10 minutes, preferably 10 seconds to 8 minutes, preferably 30 seconds to 5 minutes, preferably 1 minute to 2 minutes, prior to the measuring. Of course, longer or shorter contacting times may also be employed, as appropriate.

Mixture

One particular advantage of the Zr-MOF of the present disclosure is its photostability in a broad pH range. The disclosed Zr-MOF maintains its fluorescence emissions intensity, and thus can be employed for the detection of copper cations and/or chromate anions, in pH conditions ranging from 2 to 11, preferably 3 to 10, preferably 4 to 9, preferably 5 to 8, preferably 6 to 7. Therefore, the use of buffers is not a requirement in the methods herein. However, in some embodiments, a buffer may be optionally added to the fluid sample to ensure the resulting mixture has a suitable pH. The buffer may be optionally added to the fluid sample to provide a concentration in the mixture of 1 to 50 mM, preferably 2 to 45 mM, preferably 3 to 40 mM, preferably 4 to 35 mM, preferably 5 to 30 mM, preferably 6 to 25 mM, preferably 7 to 20 mM, preferably 8 to 15 mM, preferably 9 to 12 mM, preferably 10 to 11 mM, based on a total volume of the mixture.

The buffer may be a phosphate buffer, a borate buffer, a citrate buffer, an acetate buffer, a sulfonic acid buffer (in particular a zwitterionic sulfonic acid buffer), an amino alcohol-based buffer, an arsenate buffer, as well as mixtures thereof. Specific examples of buffers that may be utilized herein include, but are not limited to, monosodium phosphate, monopotassium phosphate, disodium phosphate, citric acid, acetic acid, borate, N-cyclohexyl-2-aminoethanesulfonic acid (CHES), tris(hydroxymethyl)methylamino] propanesulfonic acid (TAPS), 2-(bis(2-hydroxyethyl)amino) acetic acid (bicine), tris(hydroxymethyl)aminomethane) (tris), 3-[N-tris(hydroxymethyl)methylamino]-2-hydroxypropanesulfonic acid (tricine), 34N-tris(hydroxymethyl) methylamino]-2-hydroxypropanesulfonic acid (TAPSO), 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), piperazine-N,N'-bis(2-ethanesulfonic acid) (MOPS), piperazine-N,N'-bis(2-ethanesulfonic acid) (PIPES), dimethylarsenic acid (cacodylate), 2-(N-morpholino)ethanesulfonic acid (MES), bis-tris methane, N-(2-acetamido)iminodiacetic acid (ADA), N-(2-acetamido)-2-aminoethanesulfonic acid (ACES), 3-morpholino-2-hydroxypropanesulfonic acid (MOPSO), cholamine chloride hydrochloride, triethanolamine, 3-[4-(2-hydroxyethyl)piperazin-1-yl]propane-1-sulfonic acid (HEPPS), N-(2-hydroxyethyl)piperazine-N'-(4-butanesulfonic acid) (HEPBS), aminomethyl propanol (AMP), including mixtures thereof. In preferred embodiments, the buffer is 4-(2-hydroxyethyl)-1-piperazineethanesulfonic acid (HEPES).

Another particular advantage of the Zr-MOF of the present disclosure is its photostability under a broad range of temperatures. It has been found that the disclosed Zr-MOF maintains its fluorescence emissions intensity, and thus can be employed for the detection of copper cations and/or chromate anions, in mixtures having a temperature ranging from 5 to 85° C., preferably 10 to 80° C., preferably 15 to 75° C., preferably 20 to 70° C., preferably 25 to 65° C., preferably 30 to 60° C., preferably 35 to 55° C., preferably 40 to 50° C.

Another particular advantage of the Zr-MOF of the present disclosure is its stability and effectiveness after being recycled. For example, after contacting, the Zr-MOF may be collected and recycled by subjection to a chelating agent (e.g., EDTA) and drying to form a recycled Zr-MOF. The recycled Zr-MOF may have substantially no variation in fluorescence intensity and/or sensitivity/selectivity towards copper cations and/or chromate anions when compared to a pristine sample of Zr-MOF.

Measurements

The detection of copper cations and/or chromate anions in the fluid sample can be accomplished using fluorescence emissions techniques.

In some embodiments, after forming the mixture, a fluorescence emission profile of the mixture is measured at an excitation wavelength ($\lambda_{exe}$) of 360 nm to determine a presence or absence of copper cations and/or chromate anions in the fluid sample. In some embodiments, the Zr-MOF has a fluorescence emissions peak at 480 to 500 nm, preferably 482 to 498 nm, preferably 484 to 496 nm, preferably 486 to 494 nm, preferably 488 to 492 nm, preferably 491 nm, when excited at an excitation wavelength of 360 nm. The fluorescence emissions peak has a maximum intensity in the absence of copper cations/chromate anions, and, upon being exposed to copper cations and/or chromate anions, a reduction of the intensity of the fluorescence emission peak ensues.

In some embodiments, the method may first involve measuring or otherwise obtaining a fluorescence emission profile of the Zr-MOF in a blank sample (which contains no copper cations/chromate anions) of equal volume to the fluid sample volume to be tested. Then, after contacting the Zr-MOF with the fluid sample to form the mixture, the fluorescence emission profile of the mixture can be measured and directly compared to that obtained from the blank sample. Such a comparative analysis may advantageously provide accurate and reliable copper/chromate ion detection.

Therefore, the presence of copper cations and/or chromate anions in the fluid sample may be indicated by measuring or monitoring for a reduced intensity of the fluorescence emission peak associated with the Zr-MOF, for example, by comparing the measured intensity to that of a blank sample in which no copper cations and/or chromate anions are present. If the intensity of the fluorescence emission peak (e.g., at 480 to 500 nm) of the mixture is the same or substantially the same (e.g., intensity difference of 2% or less, 1% or less, 0.5% or less, 0.1% or less) as that of the blank sample, then it can be determined that no copper cations and/or chromate anions are present in the mixture (and thus the fluid sample). On the other hand, if the intensity of the fluorescence emission peak (e.g., at 480 to 500 nm) of the mixture is reduced (e.g., intensity is reduced by more than 2%, more than 3%, more than 4%, more than 5%, more than 10%, more than 15%, more than 20%, more than 30%, etc.) compared to that of the blank sample, then it can be determined that copper cations and/or chromate anions are present in the mixture (and thus the fluid sample).

In some embodiments, the method further involves determining/quantifying a concentration of the copper cations and/or chromate anions in the fluid sample. This may be accomplished by measuring a normalized fluorescence emission, defined as $$(I_0-I)/(I_{max}-I_{min})$$

where $I_0$ is a maximum fluorescence intensity of the Zr-MOF in a blank sample devoid of copper cations and/or chromate anions, I is a maximum fluorescence intensity of the mixture, and $I_{max}$ and $I_{min}$ represent the highest and lowest recorded fluorescence intensity values, respectively. For example, an initial fluorescence intensity readout ($I_0$) of the emissions peak at 480 to 500 nm of the Zr-MOF in a blank sample may be obtained, then the fluid sample may be titrated into the Zr-MOF to form the mixture, and the fluorescence intensity of the emissions peak at 480 to 500 nm may be measured after each addition (I). The normalized fluorescence emission of the mixture $[(I_0-I)/(I_{max}-I_{min})]$ after each addition may be plotted as a function of concentration, and the concentration of copper cations and/or chromate anions in the fluid sample may then be calculated by comparing the plot to a calibration curve formed using known concentrations of copper cations and/or chromate anions, as is known to those of ordinary skill in the art.

The methods of the present disclosure are preferably selective for the detection of copper cations and/or chromate anions, that is, only the presence of copper cations and/or chromate anions in the mixture produces a reduced intensity readout at the fluorescence emission peak around 480 to 500 nm. For example, cations other than copper which may be present in the fluid sample, including but not limited to, cations of sodium, potassium, calcium, magnesium, barium, strontium, rubidium, cesium, iron (ferrous and ferric), arsenic, cobalt, manganese, nickel, palladium, zinc, cadmium, mercury, silver, aluminum, gallium, chromium, lead, and mixtures thereof, do not cause a substantial fluorescence intensity reduction when combined with the Zr-MOF. For example, such non-copper cations reduce the measured intensity by 20% or less, preferably 15% or less, preferably 10% or less, preferably 5% or less, preferably 1% or less, preferably 0.5% or less, preferably 0.1% or less, even when present at 100-fold higher concentrations (or more) than copper. Anions other than chromate anions which may be present in the fluid sample, including but not limited to, chloride, carbonate, bicarbonate, sulfate, bromide, iodide, acetate, hydroxide, sulfide, hydrosulfide, chlorate, fluoride, hypochlorite, nitrate, nitrite, perchlorate, peroxide, phosphate, phosphite, sulfite, hydrogen phosphate, hydrogen sulfate (bisulfate), and permanganate, and mixtures thereof, do not cause a substantial fluorescence intensity reduction when combined with the Zr-MOF. For example, such non-chromate anions reduce the measured intensity by 2% or less, preferably 1.5% or less, preferably 1.0% or less, preferably 0.5% or less, preferably 0.1% or less, preferably 0.05% or less, preferably 0.01% or less, even when present at 100-fold higher concentrations (or more) than chromate anions.

In some embodiments, non-copper cations produce a normalized fluorescence emission of less than 0.2, preferably less than 0.15, preferably less than 0.1, preferably less than 0.05, preferably less than 0.01, when present in the mixture in a concentration of 0.1 M. In some embodiments, non-chromate anions produce a normalized fluorescence emission of less than 0.1, preferably less than 0.05, preferably less than 0.04, preferably less than 0.03, preferably less than 0.02, preferably less than 0.01 when present in the mixture in a concentration of 0.1 M. Whereas copper cations and/or chromate anions, when present in the mixture at a concentration of 0.1 M, preferably produce a normalized fluorescence emission of at least 0.6, preferably at least 0.65, preferably at least 0.7, preferably at least 0.75, preferably at least 0.8, preferably at least 0.85, preferably at least 0.9, preferably at least 0.95, and up to 1.0. The change in normalized fluorescence emission between copper/chromate ions and non-copper/chromate ions enables extremely accurate and facile copper/chromate ion detection and/or copper/chromate ion concentration determination, even in the presence of various other cations.

Recycling

After contacting and measuring, the methods may also involve recycling the Zr-MOF. Recycling may be accomplished by washing the zirconium metal-organic framework with a chelating agent to remove any adsorbed copper/chromate ions. Suitable chelating agents may include, but are not limited to, ethylene diamine tetraacetic acid (EDTA), diethylene triamine pentaacetic acid (DPTA), hydroxyethylene diamine triacetic acid (HEDTA), ethylene diamine di-Ortho-hydroxy-phenyl acetic acid (EDDHA), ethylene diamine di-ortho-hydroxy-para-methyl phenyl acetic acid (EDDHMA), ethylene diamine di-ortho-hydroxy-para-carboxy-phenyl acetic acid (EDDCHA). Preferably EDTA is used as the chelating agent. The Zr-MOF may be washed with the chelating agent for example a 0.1 to 5 M aqueous solution, preferably 0.5 to 2.5 M aqueous solution, preferably 1 to 1.5 M aqueous solution.

Then, the Zr-MOF may optionally be washed with water, then dried at 70 to 130° C., preferably 80 to 120° C., preferably 90 to 110° C., preferably 100° C. for 30 to 90 minutes, preferably 45 to 80 minutes, preferably 60 to 70 minutes, preferably under vacuum, to form a recycled Zr-MOF. The recycled Zr-MOF may have substantially no variation in fluorescence intensity and/or sensitivity/selectivity towards copper cations and/or chromate anions when compared to a pristine sample of Zr-MOF, even after being used and recycled for 2 or more cycles, preferably for 3 or more cycles, preferably for 4 or more cycles, preferably for 5 or more cycles.

The examples below are intended to further illustrate protocols for preparing the Zr-MOF and for detecting copper cations and/or chromate anions in fluid samples using the Zr-MOF, and are not intended to limit the scope of the claims.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

EXAMPLES

Results and Discussion

Characterization of the Linker $H_2L$

Figure 10:
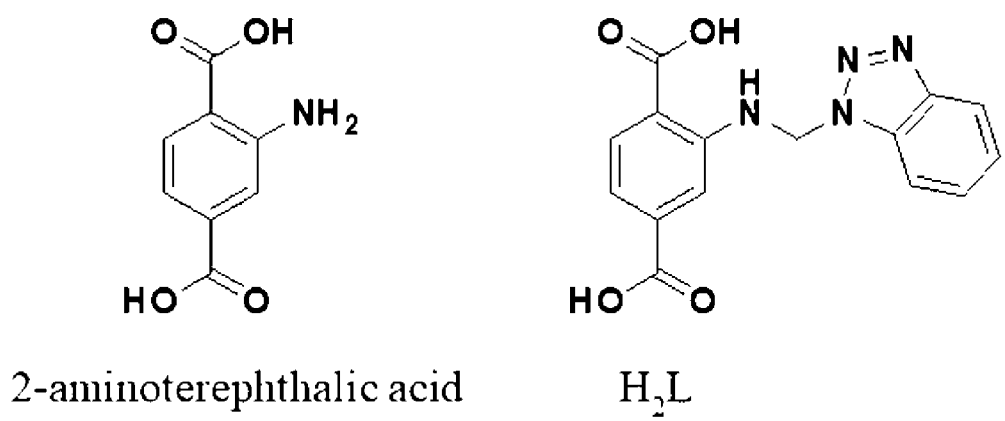
FIG. 10 illustrates the structures of 2-aminoterephthalic acid (2-amino-1,4-benzenedicarboxylic acid, $NH_2$—BDC) and 2-(((1H-benzo[d][1,2,3]triazol-1-yl)methyl)amino)tere-phthalic acid ($H_2L$)
Figure 11:
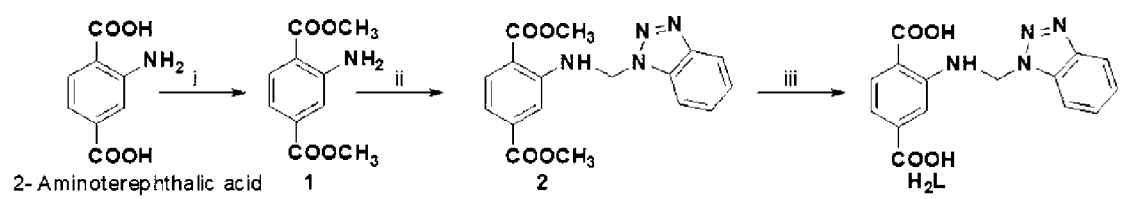
FIG. 11 illustrates the synthesis of $H_2L$ where (i) MeOH, HCl (cat.), reflux, 12 h; (ii) HCHO solution, EtOH, benzotriazole, r.t., 24 h; (iii) EtOH, KOH, reflux, 12 h.

The 2-aminoterephthalic acid linker has been presynthetically modified herein by appendage of a benzotriazole moiety to give $H_2L$ (FIG. 10). This new linker was synthesized by reacting methyl ester of 2-aminoterephthalic acid (1) with benzotriazole in the presence of formaldehyde to give 2 followed by deprotection of the diacid by alkaline hydrolysis to give $H_2L$ in good yield as shown in FIG. 11. The structures of 2 and $H_2L$ were confirmed by $^1H$ NMR, $^{13}C$ NMR, and elemental analyses data.

Characterization of UiO-66-$NH_2$ and UiO-66-NH-BT

The powdered XRD pattern of UiO-66-$NH_2$, was consistent with that reported in the literature (FIG. 1). See A. Kumar, M. K. Ghosh, C.-H. Choi, H.-S. Kim, RSC Adv. 5 2015 23613-23621, incorporated herein by reference in its entirety. UiO-66-NH-BT (UiO-66 type MOF prepared using $H_2L$ as the linker) was also synthesized with the same high crystallinity and characteristic peaks of UiO-66-$NH_2$ at 2θ=7.78°, 8.92° (FIG. 1). This establishes that functionalization of the aminoterephthalic acid with benzotriazole did not disturb the framework and connectivity of UiO-66-$NH_2$.

Figure 2:
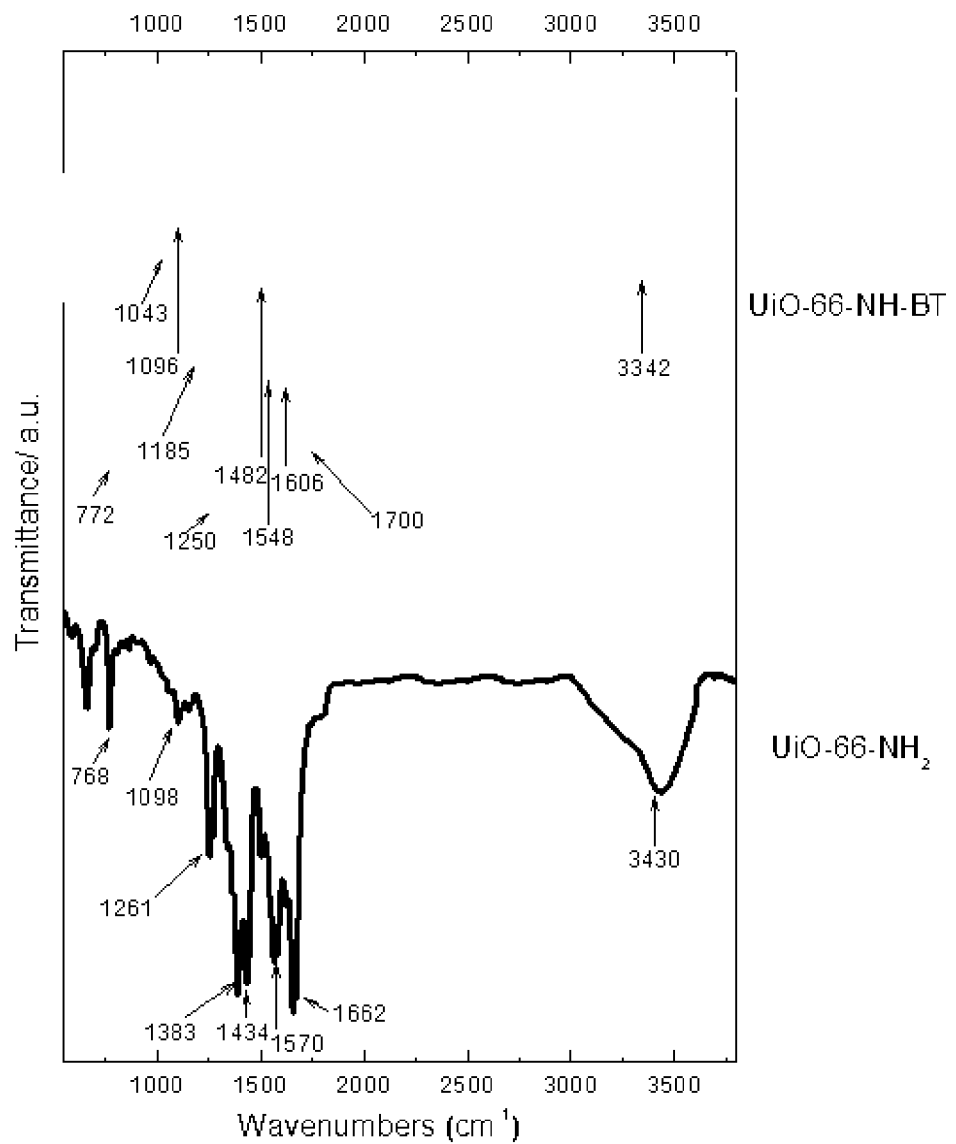
FIG. 2 illustrates the FTIR spectra of UiO-66-NH-BT (top) and UiO-66-$NH_2$ (bottom)

The IR spectrum of UiO-66-$NH_2$ (FIG. 2) shows the characteristic peak at 768 that is assigned to the stretching vibration of the C—H bond in the benzene ring, the peaks at 1261 and 1383 $cm^{-1}$, corresponds to the vibrations of the bonding between aromatic carbon and nitrogen of the amine of the 2-amino terephthalate. The bands at 1434-1570 $cm^{-1}$ indicates the presence of amino carboxylate compounds that were coordinated with the zirconium metal center. The peaks at 1570 and 1662 $cm^{-1}$ represent —COO asymmetrical stretching and the peaks at 1383 and 1434 $cm^{-1}$ —COO symmetrical stretching. The broad peak at 3430 $cm^{-1}$ represent the symmetric and asymmetric vibrations of $NH_2$ of the organic linker. The spectrum of UiO-66-NH-BT shows a sharp peak at 772 that represents the stretching vibration of the C—H bond in the two benzene rings. The two peaks at 1043 and 1096 $cm^{-1}$ indicate the stretching vibration of N—C, indicating that there are two adjacent N—C bonds on the benzene ring of the benzotriazole. The peak at 1250 $cm^{-1}$ is strong, representing the stretching vibration of —N=N— of the benzotriazole. The rest of the peaks at 1295, 1349, 1423, 1482, 1548, 1606, and 1700 $cm^{-1}$ are assigned to the vibrations of the bond between aromatic carbon and nitrogen of the amine, asymmetrical and symmetrical stretching of —COO. The broad peak at 3342 $cm^{-1}$ corresponds to the symmetric and asymmetric vibrations of NH bond of the organic linker.

Figure 3:
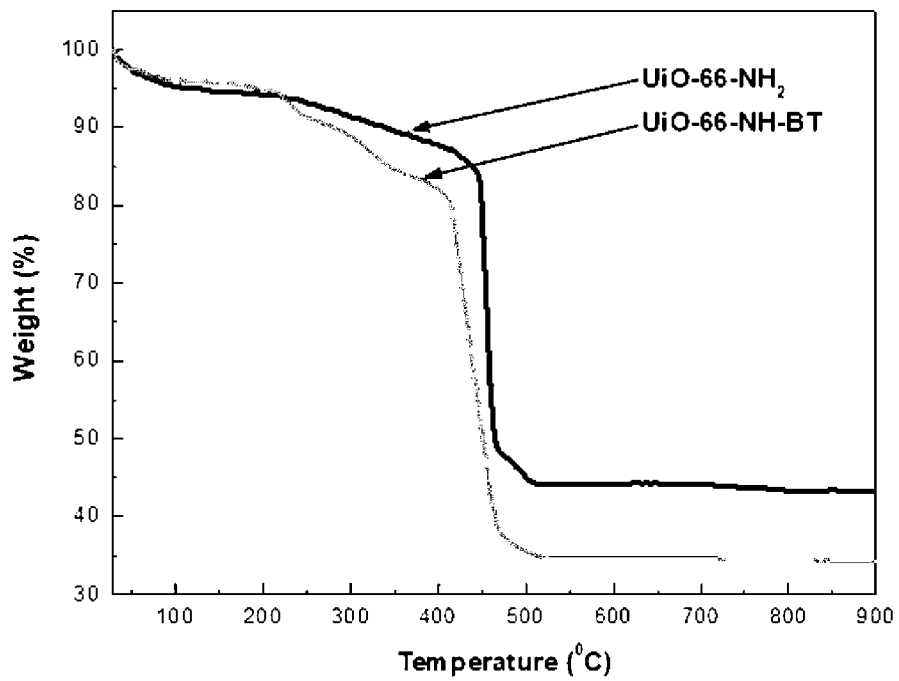
FIG. 3 illustrates the TGA of UiO-66-NH-BT and UiO-66-$NH_2$.
Figure 4:
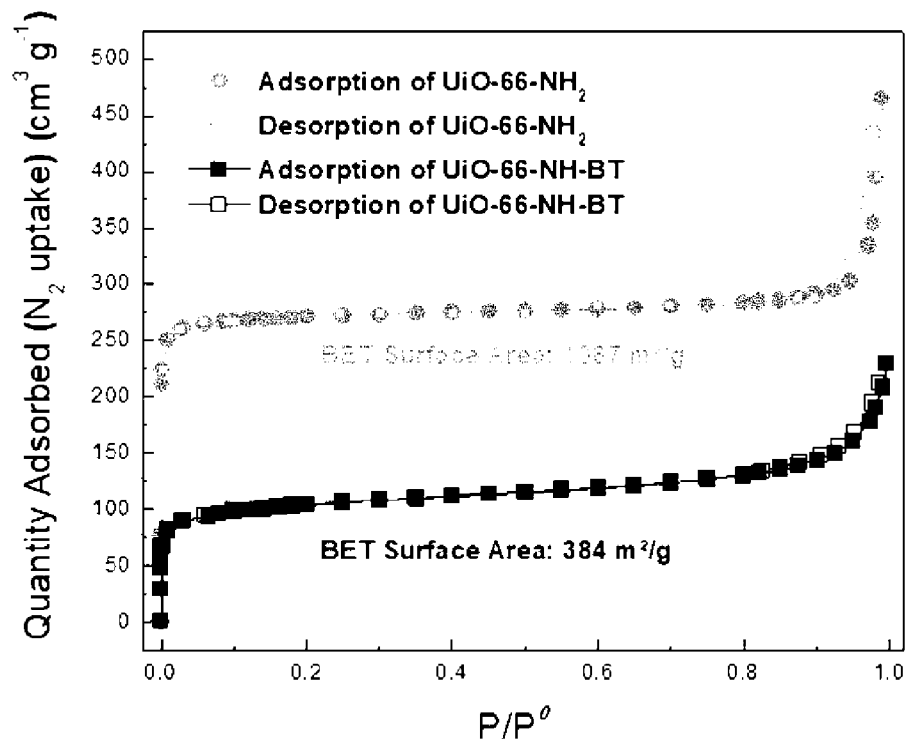
FIG. 4 illustrates the $N_2$ adsorption isotherms of UiO-66-NH-BT and UiO-66-$NH_2$, where the filled and open circles represent the adsorption and desorption branches, respectively.

The thermal stability of the UiO-66-$NH_2$ and UiO-66-NH-BT materials, were measured by thermogravimetric analysis (TGA) under an air flow with a heating rate of 5° C. $min^{-1}$ (FIG. 3). Both samples show identical thermal behavior with the initial mass loss of 5.3% and 4.3% for UiO-66-$NH_2$ and UiO-66-NH-BT below 150° C. This mass loss was assigned to the removal of trapped solvents molecules from the pores of the structure. The total weight loss for UiO-66-$NH_2$ and UiO-66-NH-BT were 46.5% and 48.5% respectively, which occurs at a temperature of 410° C. indicating that both MOFs are stable up to 410° C. The final residue was 44.3% and 34.7% for UiO-66-$NH_2$ and UiO-66-NH-BT respectively which corresponds to the zirconium oxides. These results clearly indicate that the introduction of the benzotriazole functional groups does not influence the thermal stability. Nitrogen sorption experiments of UiO-66-NH-BT showed that it is Type I. The BET surface area and the pore volume of UiO-66-NH-BT was found to be 384 $m^2$ $g^{-1}$ and 0.275 $cm^3$ $g^{-1}$ respectively. These were very small as compared to the pristine UiO-66-$NH_2$ (BET surface area=1067 $m^2$ $g^{-1}$ and pore volume=0.517 $cm^3$ $g^{-1}$) due to the presence of the appended benzotriazole moieties that block the pores and reduced the surface area (FIG. 4).

Optical Properties of UiO-66-NH-BT

The emission studies of UiO-66-NH-BT was carried out in aqueous solution as an emulsion. The emission spectrum showed that UiO-66-NH-BT produces a peak at 491 nm (FIG. 5) which is 42 nm red shifted from the emission peak of UiO-66-NH$_2$ ($\lambda_{em}$=449 nm) at an excitation wavelength of 360 nm. This indicates that on excitation at 360 nm electron transfer (ET) from the benzotriazole ring to the main structural framework of UiO-66 produces a redshifted and an enhanced emission at 491 nm in case of UiO-66-NH-BT. See Sanda, S.; Parshamoni, S.; Biswas, S.; Konar, S. Highly Selective Detection of Palladium and Picric Acid by a Luminescent MOF: A Dual Functional Fluorescent Sensor. *Chem. Commun.*, 2015, 51, 6576-6579; and Li, H.; Fan, J.; Hu, M.; G. Cheng, G.; Zhou, D.; Wu, T.; Song, F.; Sun, S.; Duan, C.; X. Peng, X. Highly Sensitive and Fast-Responsive Fluorescent Chemosensor for Palladium: Reversible Sensing and Visible Recovery. *Chem.-Eur. J.*, 2012, 18, 12242, each incorporated herein by reference in their entirety.

Cation Sensing Properties of UiO-66-NH-BT

In order to check the cation sensing properties, UiO-66-NH-BT was screened with different cations and the change in its absorbance and emission properties were noted. It was found that on addition of different cations only copper ion produces a change in the emission of UiO-66-NH-BT. All the optical sensing measurements were performed using $10^{-2}$M aqueous solutions of $Cu^{2+}$.

Figure 5:
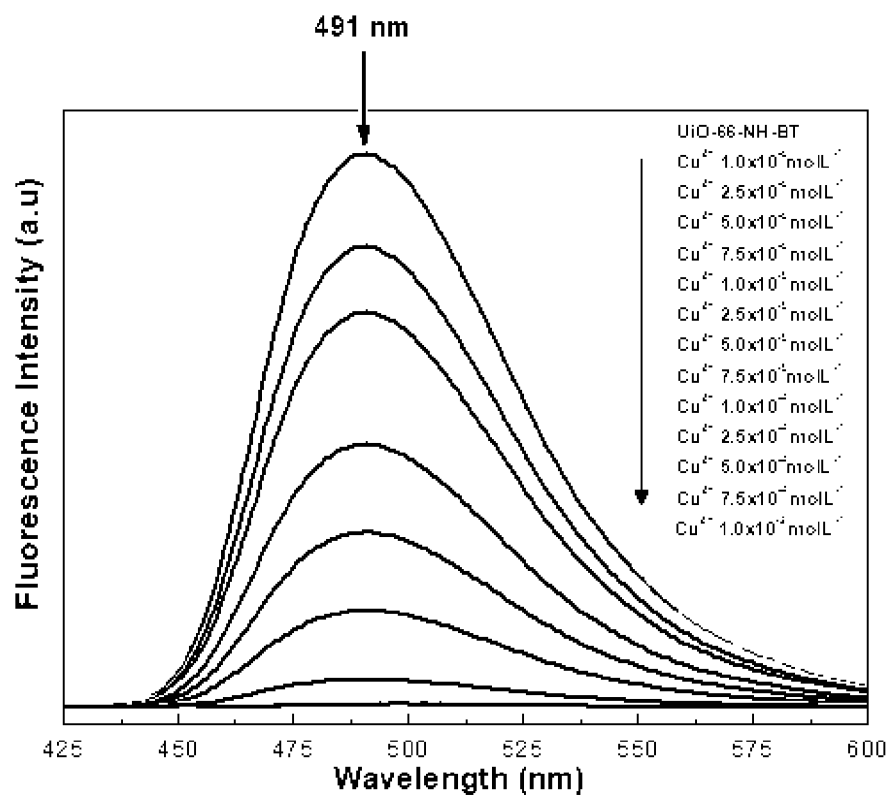
FIG. 5 illustrates the changes in fluorescence emission spectra of UiO-66-NH-BT with the incremental addition of $Cu(NO_3)_2$ ($10^{-2}$M) in water ($\lambda_{exe}$=360 nm)
Figure 6:
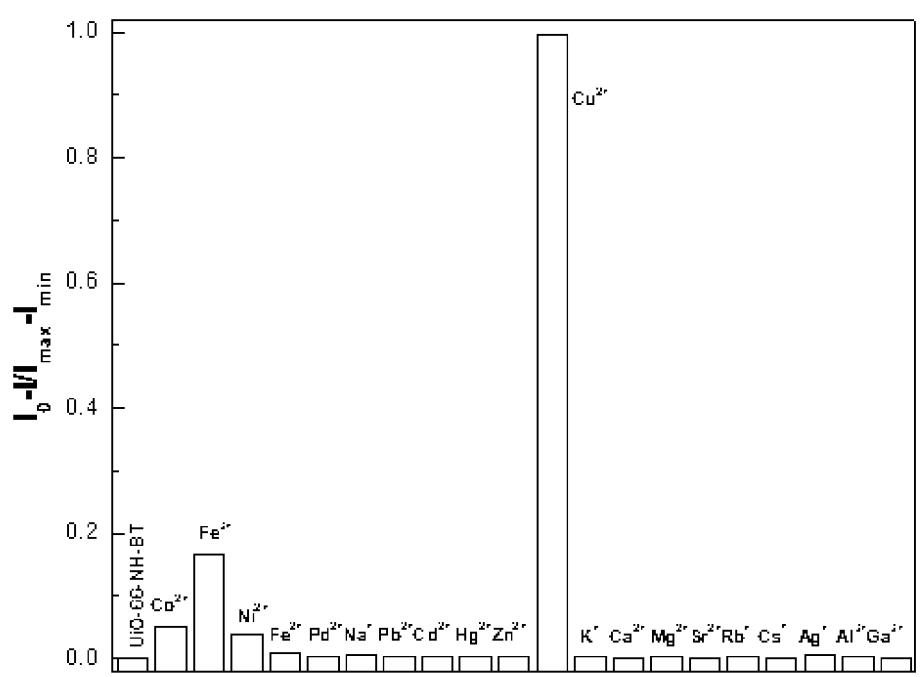
FIG. 6 illustrates the change in the normalized fluorescence emission of UiO-66-NH-BT in water upon addition of 200 μL of different metal cations ($10^{-2}$M)

In order to further understand the chemosensing properties of UiO-66-NH-BT, the changes in the fluorescence emission intensity were examined as a function of increasing $Cu^{2+}$ concentration at an excitation wavelength of 360 nm. The emission was quantitatively quenched with increasing concentrations of $Cu^{2+}$ and was observed to be completely quenched when a 1:1 UiO-66-NH-BT: $Cu^{2+}$ molar ratio was achieved (FIG. 5). The quenching efficiency was then elucidated by calculating the Stern-Volmer constant. From the titration curve, the Stern-Volmer constant, $K_{SV}$, was calculated to be $1.1 \times 10^5$. The sensitivity of UiO-66-NH-BT towards $Cu^{2+}$ was determined from the calculated detection limit which was found to be 0.3 µM. The selectivity and tolerance of UiO-66-NH-BT towards $Cu^{2+}$ as compared to other metal contaminants was investigated by immersion of UiO-66-NH-BT in solutions of different metal ions (e.g. $Na^+$, $K^+$, $ca^{2+}$, $Mg^{2+}$, $Sr^{2+}$, $Rb^{2+}$, $Cs^{2+}$, $Fe^{2+}$, $Fe^{3+}$, $Co^{2+}$, $Cu^{2+}$, $Ni^{2+}$, $Zn^{2+}$, $Cd^{2+}$, $Hg^{2+}$, $Pd^{2+}$, $Ag^+$, $Al^{3+}$, $Ga^{3+}$, and $Pb^{2+}$) (FIG. 6). As shown in FIG. 6, emission remained the same for all metal ions tested, except for $Cu^{+2}$ where the emission was completely quenched. This high selectivity for $Cu^{2+}$ ion is due to the fact that copper occurs highest on the Irving-Williams series that leads to coordinative interactions with different energies as compared to other metal ions. To explore the possibility of using UiO-66-NH-BT in a practical purpose, competitive binding experiments with to 200 µL of different metal ions ($10^{-2}$ M) in the presence of 200 µL $Cu^{2+}$ ion was carried out which exhibited that they did not interfere with the quenching of UiO-66-NH-BT by $Cu^{2+}$.

Anion Sensing Properties of UiO-66-NH-BT

Figure 7:
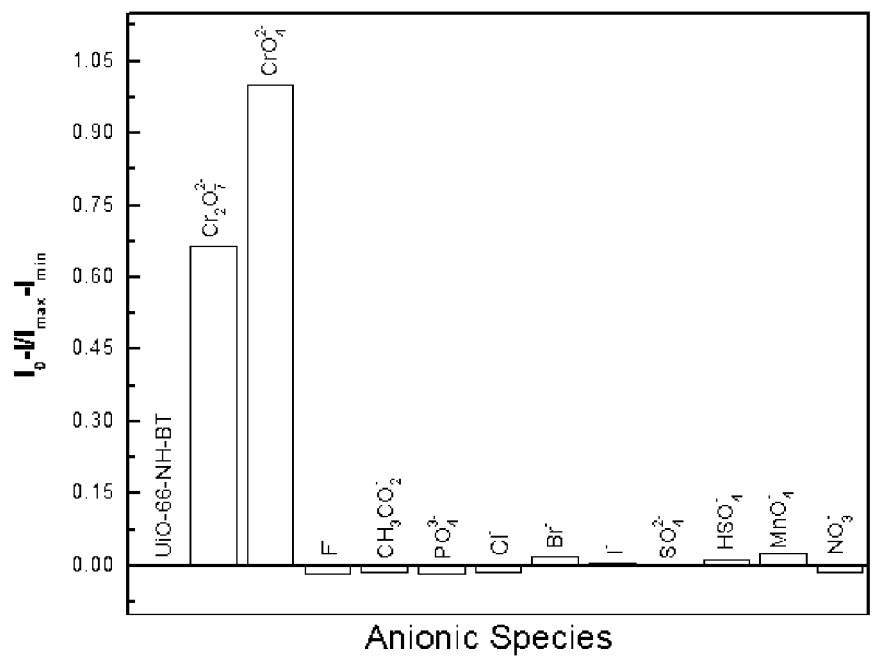
FIG. 7 illustrates the change in the normalized fluorescence emission of UiO-66-NH-BT in water upon addition of 200 μL of different anionic species ($10^{-2}$M)

Anion sensing properties of UiO-66-NH-BT was also investigated with the aqueous potassium salts solutions ($10^{-2}$ M) of the anions, $F^-$, $Cl^-$, $Br^-$, $I^-$, $CH_3CO_2^-$, $NO_3^-$, $SO_4^{2-}$, $HSO_4^-$, $PO_4^{3-}$, $MnO_4^-$, $CrO_4^{2-}$, and $Cr_2O_7^{2-}$ in water (FIG. 7). Screening with these anions showed that optical properties of UiO-66-NH-BT are selectively sensitive to $CrO_4^{2-}$, and $Cr_2O_7^{2-}$ anions.

Figure 8:
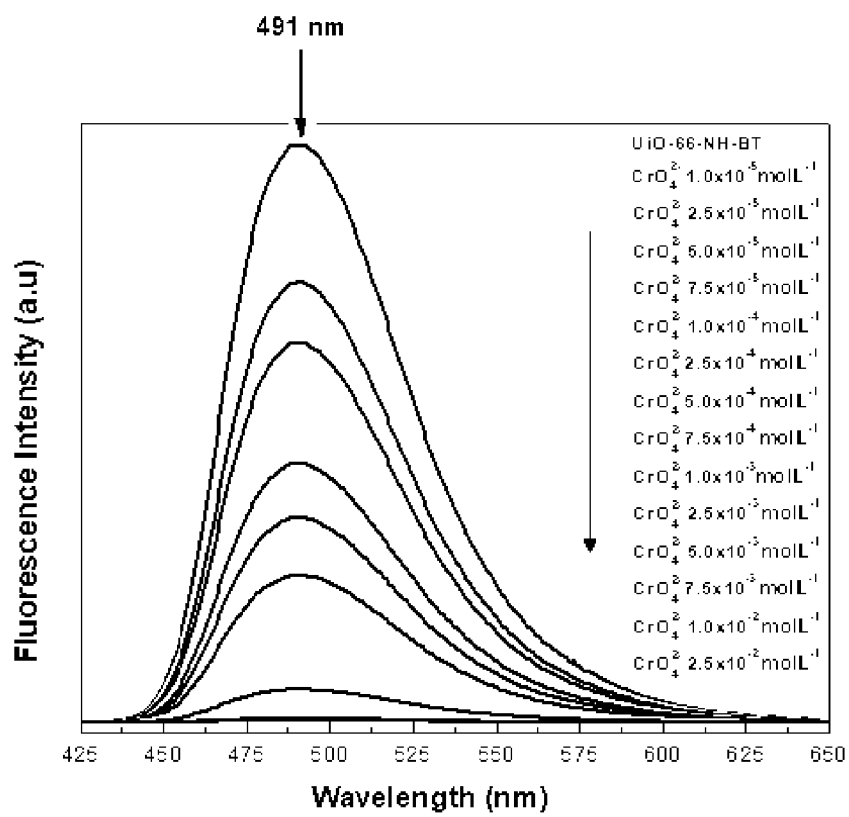
FIG. 8 illustrates the changes in fluorescence emission spectra of UiO-66-NH-BT with the incremental addition of $K_2CrO_4$ ($10^{-2}$ M) in water ($\lambda_{exe}$=360 nm)

The fluorescence emission spectroscopy analysis of UiO-66-NH-BT with the chromium oxyanions showed that $Cr_2O_7^{2-}$ ion produces partial quenching while the $CrO_4^{2-}$ ion produce a complete quenching of the emission spectra indicating that a partial and full complexation was realized between the chromate oxyanions and the benzotriazole that consequently inhibits the electron transfer to the benzene ring of the main framework of UiO-66. The quenching constant $K_{sv}$ calculated for $Cr_2O_7^{2-}$ and $CrO_4^{2-}$ were $3.9 \times 10^3$ and $6.7 \times 10^3$ respectively (FIG. 8). The sensitivity of UiO-66-NH-BT towards the chromium oxyanions ($Cr_2O_7^{2-}$ and $CrO_4^{2-}$) were calculated to be 11 µM and 4 µM respectively. In order to check the selectivity of the material it was tested with aqueous solutions of different anions. It was found that only the chromium oxyanions ($Cr_2O_7^{2-}$ and $CrO_4^{2-}$) caused quenching of the emission of UiO-66-NH-BT. This was mainly due to the binding of chromium with the nitrogen of the benzotriazole ring and the NH moiety of the terephthalic acid. The competitive binding experiments showed that none of the anions interfere with the quenching effects of $Cr_2O_7^{2-}$ and $CrO_4^{2-}$ even when added in excess.

Reusable Properties of UiO-66-NH-BT

Figure 9:
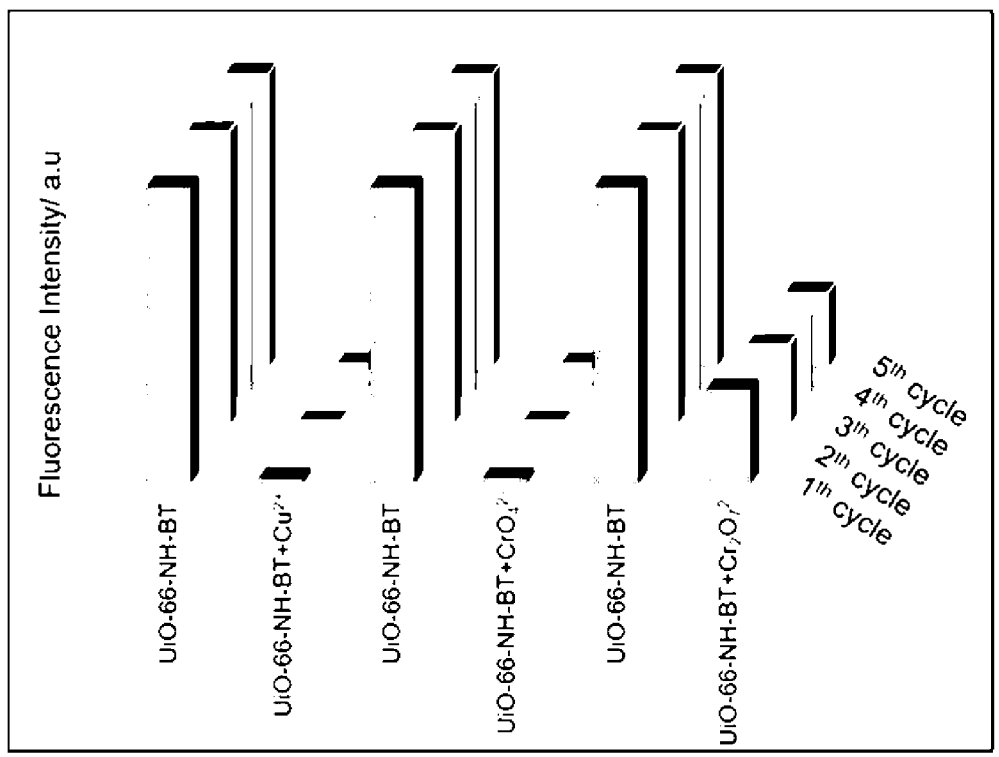
FIG. 9 is a bar diagram depicting the recyclability of UiO-66-NH-BT for fluorescence quenching experiment with $Cu^{2+}$ and chromium oxyanions up to 5 cycles.

In order to measure the recyclable sensing ability of UiO-66-NH-BT the fluorescence sensing experiments were repeated with the same materials recovered after the first set of experiments followed by washing with 1.0 M EDTA solution in water, water, and then drying at 100° C. for 1 hour. The recovered UiO-66-NH-BT showed no significant variation in the fluorescence intensities and sensitivity towards sensing of ions for five consecutive cycles (FIG. 9).

Thus, a new linker ($H_2L$) having an appended benzotriazole group was used to develop isoreticular MOF UiO-66-NH-BT. The presynthetic incorporation of the benzotriazole moiety in the UiO-66-NH$_2$ framework not only enhanced its absorption and emission properties but also introduce additional coordinating sites that help in the selective and sensitive detection of $Cu^{2+}$ and $CrO_4^{2-}/Cr_2O_7^{2-}$ ions in aqueous solutions. UiO-66-NH-BT has a quenching constant ($K_{sv}$) for $Cu^{2+}$, $Cr_2O_7^{-2}$, $CrO_4^{-2}$ of $1.1 \times 10^5$, $3.9 \times 10^3$, and $6.7 \times 10^3$ respectively with a detection limit of 0.3 µM, 11 µM and 4 µM for $Cu^{2+}$, $Cr_2O_7^{-2}$, and $CrO_4^{-2}$ respectively.

Experimental

Synthesis:

Synthesis of Compound $H_2L$: A solution of 2-aminoterephthalic acid (500 mg, 2.8 mmol) in methanol (10 mL) and 2 drops of HCl was refluxed for 10 h. The solvent was removed under vacuum and the residue was diluted with water and extracted with $CH_2Cl_2$. The organic layer was dried over anhydrous $Na_2SO_4$ and concentrated. The residue was purified by $SiO_2$ column chromatography (elution with EtOAc:hexane-1:3) to give 1 in 87% yield. A mixture of 1 (450 mg, 2.2 mmol), benzotriazole (255 mg, 2.2 mmol), formaldehyde (37%) (65 mg, 2.2 mmol) in Ethanol (10 mL) was stirred for 24 h. The solvent was removed under vacuum and the residue was diluted with water and extracted with ethyl acetate. The organic layer was dried over anhydrous $Na_2SO_4$ and concentrated. The residue was purified by $SiO_2$ column chromatography (elution with EtOAc:hexane-1:1) to give 2 in 70% yield. Compound 2 (300 mg, 0.9 mmol) was then refluxed with an ethanolic solution of KOH for 12 h. The solvent was removed under vacuum and the residue was diluted with water and the pH was adjusted to 5.0 by addition of HCl (1 M). The off white solid precipitated was filtered with a Buchner base washed with water and recrystallized from ethanol to give linker $H_2L$ in 80% yield. $^1$H NMR (DMSO-d$_6$) δ 6.37 (d, J=5.5 Hz, 2H), 7.20 (d, J=8.0 Hz, 1H), 7.37 (t, J=7.5 Hz, 1H), 7.53 (t, J=7.0 Hz, 1H), 7.85

(s, 1H), 7.87 (d, J=8.0 Hz, 1H), 8.00 (d, J 8.5 Hz, 1H), 8.09 (d, J=8.5 Hz, 1H), 9.07 (bs, 1H, NH), 12.95 (s, 2H, COOH); $^{13}$C NMR (DMSO-d$_6$) δ 70.71, 111.57, 113.59, 115.79, 117.66, 119.64, 124.64, 127.86, 132.50, 136.14, 145.86, 148.54, 151.68, 167.29, 169.52; Anal. Calcd for C$_{15}$H$_{12}$N$_4$O$_4$: C, 57.69; H, 3.87; N, 17.94. Found: C, 57.77; H, 3.94; N, 18.07.

UiO-66-NH$_2$: UiO-66-NH$_2$ was synthesized by dissolving ZrCl$_4$ (125 mg, 0.54 mmol) and 2-amino-1,4-benzenedicarboxylic acid (134 mg, 0.75 mmol) in DMF (20 mL) with ultrasonic vibration for 30 min then 0.5 mL of acetic acid was added. The as-obtained mixture was transferred to a 50 mL vial and heated at 393 K for 24 h. Then the vial was cooled in air to room temperature. The resulting UiO-66-NH$_2$ was washed three times with DMF (5-10 mL) using a centrifuge (10,000 rpm for 30 min), and then sequentially immersed in methanol (5-10 mL three times per day) for three 24 h periods. Finally, UiO-66-NH$_2$ was activated by removing the solvent under vacuum for 24 h at 100° C. FT-IR (KBr, cm$^{-1}$): 3430, 1662, 1570, 1434, 1383, 1261, 1098, 766, 663.

UiO-66-NH-BT: UiO-66-NH-BT was synthesized in a similar way as above by dissolving ZrCl$_4$ (125 mg, 0.54 mmol) and H$_2$L (2-(((1H-benzo[d][1,2,3]triazol-1-yl)methyl)amino)terephthalic acid) (234.2 mg, 0.75 mmol) in DMF (20 mL) with ultrasonic vibration for 30 min then 0.5 mL of acetic acid was added. The as-obtained mixture was transferred to a 50 mL vial and heated at 393 K for 24 h. Then the vial was cooled in air to room temperature. The resulting UiO-66-NH-BT was washed in the same way as the previous method by three times with DMF (5-10 mL) using a centrifuge (10,000 rpm for 30 min), and then sequentially immersed in methanol (5-10 mL three times per day) for three 24 h periods. Finally, UiO-66-NH-BT was activated by removing the solvent under vacuum for 24 h at 100° C. FT-IR (KBr, cm$^{-1}$): 3342, 1751, 1700, 1606, 1548, 1482, 1421, 1340, 1250, 1185, 1099, 1042, 778, 651, 582.

The invention claimed is:

1. A zirconium metal-organic framework, which is a coordination product formed between:
   zirconium ion clusters; and
   a linker that links together adjacent zirconium ion clusters;
   wherein the linker is of formula (I)

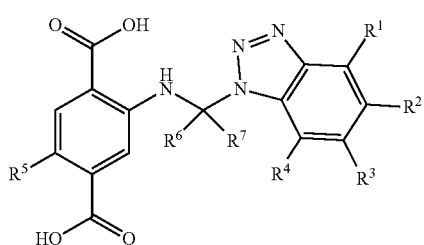

(I)

wherein:
   $R^1$ to $R^4$ are independently hydrogen, an optionally substituted alkyl, an optionally substituted aryl, an optionally substituted arylalkyl, an optionally substituted alkoxy, a hydroxyl, a carboxyl, a halo, a nitro, or a cyano,
   $R^5$ is hydrogen, an optionally substituted alkyl, an optionally substituted alkoxy, an amino, a hydroxyl, a carboxyl, a halo, a nitro, or a cyano, and
   $R^6$ and $R^7$ are independently a hydrogen or an optionally substituted alkyl group having 1 to 4 carbon atoms.

2. The zirconium metal-organic framework of claim 1, wherein $R^1$ to $R^4$ are hydrogen.

3. The zirconium metal-organic framework of claim 1, wherein $R^5$ is hydrogen.

4. The zirconium metal-organic framework of claim 1, wherein $R^6$ and $R^7$ are hydrogen.

5. The zirconium metal-organic framework of claim 1, wherein the linker is

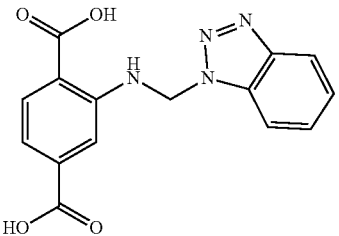

6. The zirconium metal-organic framework of claim 1, which has a zirconium ion to linker molecular ratio of 0.5:1 to 2:1.

7. The zirconium metal-organic framework of claim 1, wherein the zirconium ion clusters are of formula [Zr$_6$O$_4$(OH)$_4$]$^{12+}$.

8. The zirconium metal-organic framework of claim 1, which is isoreticular with metal-organic framework UiO-66.

9. The zirconium metal-organic framework of claim 1, which has a BET surface area of 300 to 600 m$^2$/g.

10. The zirconium metal-organic framework of claim 1, which has a pore volume of 0.2 to 0.4 cm$^3$/g.

11. The zirconium metal-organic framework of claim 1, which has a fluorescence emissions peak at 480 to 500 nm at an excitation wavelength of 360 nm.

12. A method of making the zirconium metal-organic framework of claim 1, the method comprising:
   ultrasonically mixing a zirconium(IV) salt and the linker of formula (I) in a polar aprotic solvent to form a complexation mixture;
   adding a modulator to the complexation mixture to form a modulated mixture;
   heating the modulated mixture at 100 to 150° C. for 12 to 72 hours to form a product mixture comprising the zirconium metal-organic framework; and
   separating the zirconium metal-organic framework from the product mixture.

13. The method of claim 12, wherein a concentration of the zirconium(IV) salt in the complexation mixture is 0.02 to 0.04 M, a concentration of the linker of formula (I) in the complexation mixture is 0.025 to 0.045 M, and wherein a volume ratio of the polar aprotic solvent to the modulator in the modulated mixture is 20:1 to 60:1.

14. The method of claim 12, wherein the zirconium(IV) salt is ZrCl$_4$, the polar aprotic solvent is dimethylformamide, and the modulator is acetic acid.

15. A method of detecting copper cations and/or chromate anions in a fluid sample, comprising:
   contacting the fluid sample with the zirconium metal-organic framework of claim 1 to form a mixture; and
   measuring a fluorescence emission profile of the mixture to determine a presence or absence copper cations and/or chromate anions in the fluid sample, wherein a reduction in intensity of a fluorescence emissions peak associated with the zirconium metal-organic framework indicates the presence of copper cations and/or chromate anions in the fluid sample.

16. The method of claim 15, wherein 0.001 to 10 mg of the zirconium metal-organic framework is employed per 1 mL of the fluid sample during the contacting.

17. The method of claim 15, wherein copper cations and/or chromate anions are present in the fluid sample, and wherein a concentration of copper cations and/or chromate anions in the fluid sample is from $1\times10^{-6}$ to $5\times10^{-1}$ M.

18. The method of claim 15, wherein the fluid sample is a wastewater, a tap water, a well water, or a river water, and wherein the mixture has a pH of 2 to 11 and a temperature of 10 to 70° C.

19. The method of claim 15, wherein copper cations and/or chromate anions are present in the fluid sample, and wherein the fluid sample further comprises at least one cation selected from the group consisting of cobalt, iron, nickel, palladium, sodium, lead, cadmium, mercury, zinc, potassium, calcium, magnesium, strontium, rubidium, cesium, silver, aluminum, and gallium and/or at least one anion selected from the group consisting of fluoride, acetate, phosphate, chloride, bromide, iodide, sulfate, bisulfate, permanganate, and nitrate, and the method is selective for detection of the copper cations and/or chromate anions, whereby only the presence of copper cations and/or chromate anions in the mixture produces a reduction in the intensity of the fluorescence emissions peak of greater than 20%.

20. The method of claim 15, further comprising, after the contacting and measuring, washing the zirconium metal-organic framework with a chelating agent followed by water, and then drying, to recover/recycle the zirconium metal-organic framework.

* * * * *